US010093699B2

(12) United States Patent
Cheng et al.

(10) Patent No.: US 10,093,699 B2
(45) Date of Patent: Oct. 9, 2018

(54) PEPTIDES WITH ANTIMICROBIAL, ANTICANCER AND/OR WOUND-HEALING PROMOTING ACTIVITIES, PHARMACEUTICAL COMPOSITIONS CONTAINING THE SAME, AND USE OF THE PEPTIDES WITH ANTIMICROBIAL, ANTICANCER AND/OR WOUND-HEALING PROMOTING ACTIVITIES

(71) Applicant: NATIONAL TSING HUA UNIVERSITY, Hsinchu (TW)

(72) Inventors: Jya-Wei Cheng, Hsinchu (TW); Hui-Yuan Yu, Hsinchu (TW); Hung-Lun Chu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 23 days.

(21) Appl. No.: 15/130,709

(22) Filed: Apr. 15, 2016

(65) Prior Publication Data
US 2017/0129924 A1    May 11, 2017

(30) Foreign Application Priority Data
Nov. 5, 2015    (TW) .............................. 104136447 A

(51) Int. Cl.
C07K 7/08         (2006.01)
C07K 7/06         (2006.01)
A61K 38/00        (2006.01)

(52) U.S. Cl.
CPC .................. *C07K 7/08* (2013.01); *C07K 7/06* (2013.01); *A61K 38/00* (2013.01); *Y02A 50/473* (2018.01)

(58) Field of Classification Search
None
See application file for complete search history.

(56) References Cited

U.S. PATENT DOCUMENTS

| | | | |
|---|---|---|---|
| 8,338,366 B2 | 12/2012 | Lin et al. | |
| 8,859,727 B2 | 10/2014 | Lin et al. | |
| 2010/0222268 A1 | 9/2010 | Hoffmann et al. | |

FOREIGN PATENT DOCUMENTS

| | | |
|---|---|---|
| CN | 100390194 | 5/2008 |
| TW | 201316999 | 5/2013 |
| TW | I403330 | 8/2013 |
| TW | 201520231 | 6/2015 |
| TW | 201520231 A | 6/2015 |

OTHER PUBLICATIONS

Chu et al. ("Novel Antimicrobial Peptides with High Anticancer Activity and Selectivity" PLOS ONE May 13, 2015).*
Yin et al. ("Roles of Hydrophobicity and charge Distrubution of Cationic Antimicrobial Peptides in Peptide-Membrane Interactions" The Journal of Biological Chemistry vol. 287 No. 10, pp. 7738-7745 [Mar. 2, 2012]).*
Chu et al. ("Boosting Salt Resistance of Short Antimicrobial Peptides" Antimicrobial Agents and Chemotherapy p. 1050-4052; Aug. 2013, col. 57 (8)).*
Caslo-Peptide Modification (available Aug. 24, 2012).*
Taiwan Patent Office, Office Action, Patent Applciation Serial No. 104136447, dated Sep. 26, 2016, Taiwan.
Zasloff, Michael, "Antimicrobial Peptides of Multicellular Organisms," International Weeky Journal of Science, Jan. 2002, pp. 389-395, vol. 415, Nature.com, US.
David M. Rothstein et al., "Anticandida Activity Is Retained in P-113, a 12-Amino-Acid Fragment of Histatin 5," Antimicrob Agents Chemother, May 2001, pp. 1367-1373, vol. 45, No. 5, American Society for Microbiology. US.
Hui-Yuan Yu et al., "Rational Design of Tryptophan-Rich Antimicrobial Peptides with Enhanced Antimicrobial Activities and Specificities," ChemBioChem, Nov. 2010, pp. 2273-2282, vol. 11, No. 16, Wiley-VCH Verlag GmbH & Co., Weinheim, Germany.
Robert E. Hancock et al., "Antimicrobial and Host-Defense Peptides as New Anti-Infective Therapeutic Strategies," Nature Biotechnology, Dec. 2006, pp. 1551-1557, vol. 24, No. 12, Nature Publishing Group, US.
P. La Rocca et al., "Peptide Bilayer Interactions: Simulations of Dermaseptin B, an Antimicrobial Peptide," Biophysical Chemistry, Feb. 1999, pp. 145-159, vol. 76, No. 2, Elsevier, US.
Rebecca Siegel, MPH et al. "Cancer Statistics, 2014," CA: A Cancer Journal for Clinicians, Jan./Feb. 2014, pp. 9-29, vol. 64, No. 1, American Cancer Society, US.
Fumiko Taguchi et al., "Anticancer Effects of ZD6474, a VEGF Receptor Tyrosine Kinase Inhibitor, in Gefitinib ("Iressa")—Sensitive and Resistant Xenograft Models," Cancer Sci. 2004, Dec. 2004, pp. 984-989, vol. 95, No. 12, Cancer Sci., US.
Hung-Lun Chu et al., "Boosting Salt Resistance of Short Antimicrobial Peptides," Antimicrobial Agents and Chemotherapy, Aug. 2013, pp. 4050-4052, vol. 57, No. 8, AAC, US.
Lois M. Yin et al., "Roles of Hydrophobicity and Charge Distribution of Cationic Antimicrobial Peptides in Peptide-Membrane Interactions," The Journal of Biological Chemistry, Mar. 2012, 11 pages, vol. 287, No. 10, The American Society for Biochemistry and Molecular Biology, Inc., US.
Hung-Lun Chu et al., "Novel Antimicrobial Peptides with High Anticancer Activity and Selectivity," PLoS One, May 2015, pp. 1-14, vol. 10, No. 5, PLoS, US.
Wu et al., "Peptide-based Cancer Therapy: Opportunity and Challenge," Cancer Letters, May 2014, 10 pages, Elsevier, US.
Taiwan Patent Office, Office Action, Patent Application Serial No. 104136447, dated Aug. 14, 2017, Taiwan.

* cited by examiner

*Primary Examiner* — James H Alstrum-Acevedo
*Assistant Examiner* — Tara L Martinez

(57) ABSTRACT

A peptide with antimicrobial, anticancer and/or wound-healing promoting activities is provided. The peptide with antimicrobial, anticancer and/or wound-healing promoting activities, includes: an α-helix peptide; and a short peptide consisting of about 4-10 positively charged amino acids, connected to an N-terminus of the α-helix peptide to form the peptide with antimicrobial, anticancer and/or wound-healing promoting activities, wherein the total length of the peptide with antimicrobial, anticancer and/or wound-healing promoting activities is about 10-20 amino acids.

31 Claims, 21 Drawing Sheets

Specification includes a Sequence Listing.

```
SEQUENCE LISTING

<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(2)
<223> OTHER INFORMATION: Xaa is beta-naphthylalanine

<400> SEQUENCE: 1

Xaa Xaa Lys Lys Trp Arg Lys Trp Leu Ala Lys Lys
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Xaa is beta-naphthylalanine

<400> SEQUENCE: 2

Lys Lys Lys Lys Arg Arg Xaa Xaa Lys Lys Trp Arg Lys Trp Leu Ala
1               5                   10                  15

Lys Lys

<210> SEQ ID NO 3
<211> LENGTH: 18
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Xaa is beta-naphthylalanine

<400> SEQUENCE: 3
```

```
Lys Lys Lys Lys Lys Lys Xaa Xaa Lys Lys Trp Arg Lys Trp Leu Ala
1               5                   10                  15

Lys Lys

<210> SEQ ID NO 4
<211> LENGTH: 4
<212> TYPE: PRT
<213> ORGANISM: Artificial Sequence
<220> FEATURE:
<223> OTHER INFORMATION: Chemically synthesized peptide

<400> SEQUENCE: 4

Lys Trp Trp Lys
1

<210> SEQ ID NO 5
<211> LENGTH: 10
<212> TYPE: PRT
<213> ORGANISM: Artificial Sequence
<220> FEATURE:
<223> OTHER INFORMATION: Chemically synthesized peptide

<400> SEQUENCE: 5

Lys Lys Trp Arg Lys Trp Leu Ala Lys Lys
1               5                   10
```

PEPTIDES WITH ANTIMICROBIAL, ANTICANCER AND/OR WOUND-HEALING PROMOTING ACTIVITIES, PHARMACEUTICAL COMPOSITIONS CONTAINING THE SAME, AND USE OF THE PEPTIDES WITH ANTIMICROBIAL, ANTICANCER AND/OR WOUND-HEALING PROMOTING ACTIVITIES

CROSS REFERENCE TO RELATED APPLICATION

The present application is based on, and claims priority from, Taiwan Application Serial Number 104136447, filed on Nov. 5, 2015, the disclosure of which are hereby incorporated by reference herein in its entirety.

INCORPORATION BY REFERENCE OF SEQUENCE LISTING

A sequence listing submitted as a text file via EFS-Web is incorporated herein by reference. The text file containing the sequence listing is named "0765-A53555-US_Seq_Listing.txt"; its date of creation was Jan. 5, 2016; and its size is 1,885 bytes.

TECHNICAL FIELD

The present disclosure relates to a novel peptide, and more particularly to a peptide having antimicrobial, anticancer and/or wound-healing promoting activities at the same time, a pharmaceutical composition containing the same, and a method for preparing the pharmaceutical composition.

BACKGROUND

Cationic antimicrobial peptides (CAMPs), important for regulating the innate immune system of plants, insects, and animals (Zasloff M (2002) Antimicrobial peptides of multicellular organisms. Nature 415:389-395.), are recognized as candidates against bacterium and fungi originally (Rothstein D M, Spacciapoli P, Tran L T, Xu T, Roberts F D, et al. (2001) Anticandida activity is retained in P-113, a 12-amino-acid fragment of histatin 5. Antimicrob. Agents Chemother. 45: 1367-1373; Yu H Y, Huang K C, Yip B S, Tu C H, Chen H L, et al. (2010) Rational design of tryptophan-rich antimicrobial peptides with enhanced antimicrobial activities and specificities. Chembiochem 11: 2273-2282.). CAMPs are normally characterized by their positive charges and amphipathic features, which enable them to bind to negatively charged bacterial cell membranes and cause a disruption of the membrane, hence the death of bacterium (Hancock R E and Sahl H G (2006) Antimicrobial and host-defense peptides as new anti-infective therapeutic strategies. Nat Biotechnol 24: 1551-1557.; La Rocca P, Shai Y and Sansom M S (1999) Peptide-bilayer interactions:simulations of dermaseptin B, an antimicrobial peptide. Biophys Chem 76:145-159.). The membrane lytic property of CAMPs makes them potential therapeutics for overcoming the antibiotic resistance (Yu H Y, Huang K C, Yip B S, Tu C H, Chen H L, et al. (2010) Rational design of tryptophan-rich antimicrobial peptides with enhanced antimicrobial activities and specificities. Chembiochem 11: 2273-2282.).

Although tremendous efforts have been put into the development of new treatments, cancer remains the major cause of death (Siegel R, Ma J, Zou Z and Jemal A (2014) Cancer statistics 2014. CA Cancer J Clin 64: 9-29). Chemotherapies, despite their severe side effects to normal cells and tissues, and the easy formation of multi-drug resistances, are still the principal drugs used to treat cancer in the advanced or metastatic stages (Siegel R, Ma J, Zou Z and Jemal A (2014) Cancer statistics 2014. CA Cancer J Clin 64: 9-29).

Thus, the development of new cancer drugs with low toxicity to normal cells and a new mode of mechanism that can avoid multi-drug resistance may provide a new direction for anticancer therapy.

Accordingly, at present, a new peptide drug which has hypotoxicity to normal cells and has antimicrobial and anticancer activities is needed.

SUMMARY

The present disclosure provides a peptide with antimicrobial, anticancer and/or wound-healing promoting activities, comprising: an α-helix peptide; and a short peptide consisting of about 4-10 positively charged amino acids, connected to an N-terminus of the α-helix peptide to form the peptide with antimicrobial, anticancer and/or wound-healing promoting activities, wherein the total length of the peptide with antimicrobial, anticancer and/or wound-healing promoting activities is about 10-20 amino acids.

The present disclosure also provides a pharmaceutical composition, comprising: the peptide with antimicrobial, anticancer and/or wound-healing promoting activities mentioned above; and a pharmaceutically acceptable carrier or salt, wherein the pharmaceutical composition has antimicrobial, anticancer and/or wound-healing promoting activities, and has no influence on a normal cell.

The present disclosure further provides a method for preparing a pharmaceutical composition with antimicrobial, anticancer and/or wound-healing promoting activities, comprising: providing an effective amount of the peptide with antimicrobial, anticancer and/or wound-healing promoting activities mentioned above, serving as an active ingredient, in preparation of a pharmaceutical composition with antimicrobial, anticancer and/or wound-healing promoting activities, wherein the pharmaceutical composition is capable of inhibiting a microorganism, inhibiting a cancer cell, and/or promoting wound-healing.

The present disclosure further provides method for inhibiting a microorganism, inhibiting a cancer cell, and/or promoting wound-healing, comprising: administering the foregoing pharmaceutical composition to a subject in need thereof.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1A:
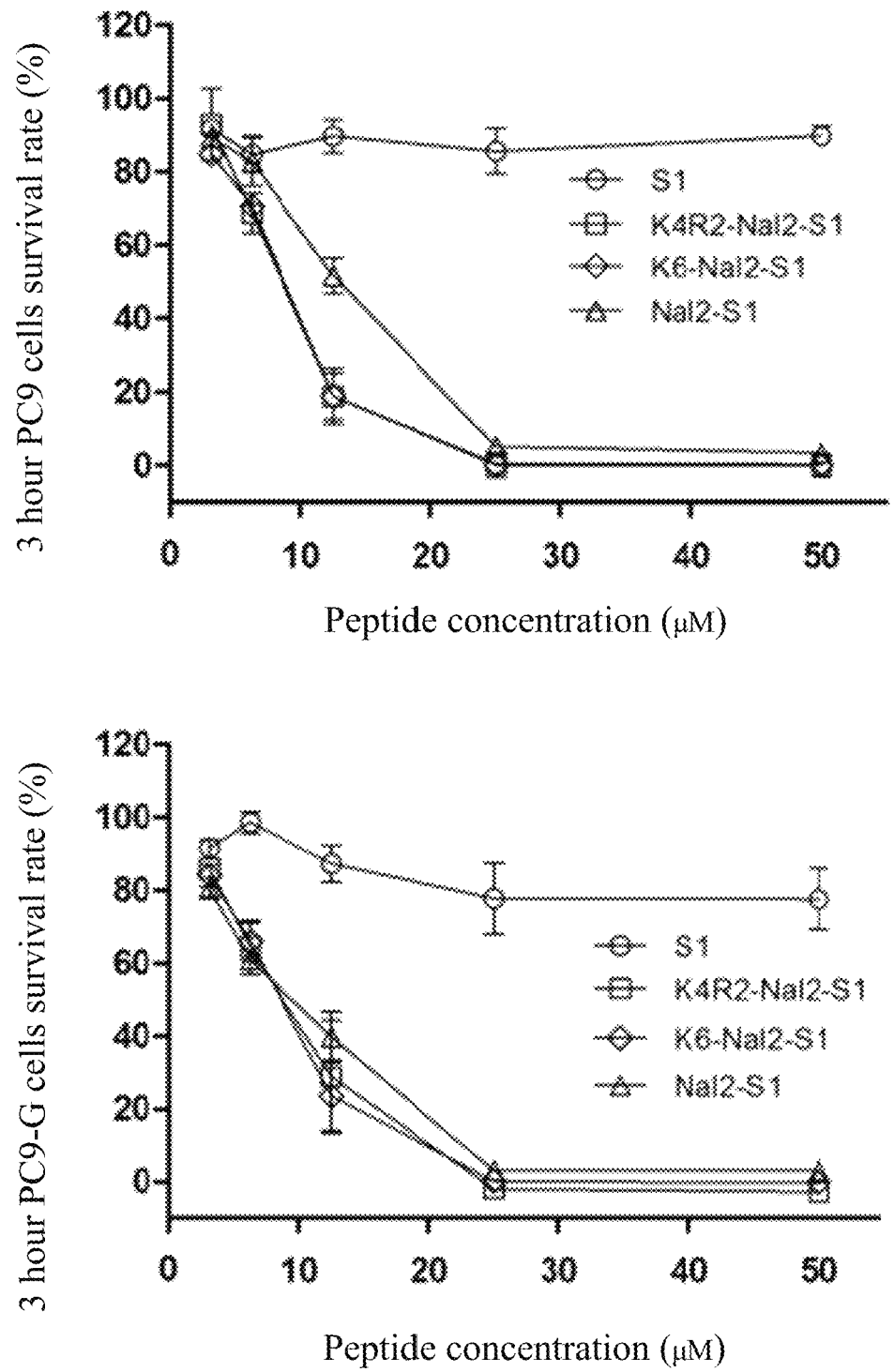
FIG. 1A shows cell survival rates of PC9 and PC9-G cells after being treated with S1, Nal2-S1, K4R2-Nal2-S1 and K6-Nal2-S1 peptides for 3 hours (the activities of S1, Nal2-S1, K4R2-Nal2-S1 and K6-Nal2-S1 against PC9 and PC9-G cell lines)

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment of the present disclosure, the present disclosure provides a novel peptide with antimicrobial, anticancer and/or wound-healing promoting activities.

The foregoing peptide with antimicrobial, anticancer and/or wound-healing promoting activities of the present disclosure, may comprise, but is not limited to an α-helix peptide and a short peptide, wherein the short peptide may consist of about 4-10 positively charged amino acids, and connect to an N-terminus of the α-helix peptide to form the foregoing peptide of the present disclosure.

The total length of the foregoing peptide of the present disclosure may be about 10 to 20 amino acids, such as 10, 11, 12, 13, 14, 15, 16, 17, 18 or 19 amino acids, but it is not limited thereto.

Amino acids which constitute the α-helix peptide have no particular limitation, and may all are natural amino acids or all are non-natural amino acids, or may comprise a natural amino acids and a non-natural amino acids at the same time, only if these amino acids can form an α-helix structure. In other words, the sequence of the α-helix peptide mentioned above has no particular limitation, only if the amino acids which constitute the sequence can form an α-helix structure.

In one embodiment, the α-helix peptide may have one or more non-natural amino acids, bit is not limited thereto. The non-natural amino acid or each of the non-natural amino acids may independently be, for example, β-naphthylalanine (Nal), (benzothien-3-yl)alanine (Bal), diphenylalanine (Dip), (4,4'-biphen-yl) alanine (Bip), (anthracen-9-yl) alanine (Ath) or (2,5,7-tri-tert-butyl-indol-3-yl) alanine (Tht), but it is not limited thereto. In one embodiment, the preceding non-natural amino acid or the non-natural amino acids may be β-naphthylalanine.

Moreover, the non-natural amino acids of the α-helix peptide mentioned above may be completely continuously arranged or partially continuously arranged. The expression "completely continuously arranged" used herein refers to in the α-helix peptide mentioned above, there is no natural amino acid between any two of the non-natural amino acids. The expression "partially continuously arranged" used herein refers to in the α-helix peptide mentioned above, for a part of the non-natural amino acids, there is no natural amino acid between any two of the non-natural amino acids, while for another part of the non-natural amino acids, an amino acid which directly connects to each non-natural amino acid is a natural amino acid.

Alternatively, the non-natural amino acids of the α-helix peptide mentioned above may be non-continuously arranged. The expression "non-continuously arranged" used herein refers to in the α-helix peptide mentioned above, an amino acid which directly connects to each non-natural amino acid is certainly a natural amino acid.

In one embodiment, the non-natural amino acids are completely continuously arranged. In this embodiment the non-natural amino acids may be located at an N-terminus of the α-helix peptide and directly connect to the short peptide, or may be located at a C-terminus of the α-helix peptide, or may be located in a middle part of the α-helix peptide.

In one specific embodiment, the non-natural amino acids are completely continuously arranged, and are located at an N-terminus of the α-helix peptide and directly connect to the short peptide. In this specific embodiment, the α-helix peptide has two non-natural amino acids, and furthermore, the two non-natural amino acids may be both β-naphthyl-alanine.

In another specific embodiment, the sequence of the α-helix peptide may comprise SEQ ID NO: 1, for example, the sequence of the α-helix peptide may consist of the sequence of SEQ ID NO: 1, but it is not limited thereto.

In addition, in the peptide with antimicrobial, anticancer and/or wound-healing promoting activities of the present disclosure, the positively charged amino acids which constitute the preceding short peptide has no particular limitation, only if is an amino acid carrying a positive charge. Each of the positively charged amino acids of the short peptide may independently be, for example, lysine, arginine or histidine, etc., but they are not limited thereto.

In one embodiment, the length of the short peptide in the peptide with antimicrobial, anticancer and/or wound-healing promoting activities of the present disclosure may be six amino acids. In this embodiment, the six positively charged amino acids which constitute the preceding short peptide may be all lysine. Alternatively, in this embodiment, the six positively charged amino acids which constitute the preceding short peptide may be a combination of 4 lysines and 2 arginines. Furthermore, in one specific embodiment, the six positively charged amino acids which constitute the preceding short peptide may be a combination of 4 lysines and 2 arginines, and from an N-terminus to the C-terminus of the short peptide, these positively charged amino acids are 4 lysines and 2 arginines in order.

Furthermore, an N-terminus of the peptide with antimicrobial, anticancer and/or wound-healing promoting activities of the present disclosure may be further acetylated. Or, a C-terminus of the peptide with antimicrobial, anticancer and/or wound-healing promoting activities of the present disclosure may be further amidated. Or, an N-terminus and a C-terminus of the peptide with antimicrobial, anticancer and/or wound-healing promoting activities of the present disclosure may be further acetylated and amidated, respectively.

In one embodiment, the sequence of the peptide with antimicrobial, anticancer and/or wound-healing promoting activities of the present disclosure may comprise the sequence of SEQ ID NO: 2 or SEQ ID NO: 3, but it is not limited thereto. In one specific embodiment, the sequence of the peptide with antimicrobial, anticancer and/or wound-healing promoting activities of the present disclosure consists of the sequence of SEQ ID NO: 2. Moreover, in another specific embodiment, the sequence of the peptide with antimicrobial, anticancer and/or wound-healing promoting activities of the present disclosure consists of the sequence of SEQ ID NO: 3.

In the specific embodiment in which the sequence of the peptide with antimicrobial, anticancer and/or wound-healing promoting activities of the present disclosure consists of the sequence of SEQ ID NO: 2, an N-terminus of the sequence of SEQ ID NO: 2 may be further acetylated. Or, in this specific embodiment, a C-terminus of the sequence of SEQ ID NO: 2 may be further amidated. Or, in this specific embodiment, an N-terminus and a C-terminus of the sequence of SEQ ID NO: 2 may be further acetylated and amidated, respectively.

Similarly, in the specific embodiment in which the sequence of the peptide with antimicrobial, anticancer and/or wound-healing promoting activities of the present disclosure consists of the sequence of SEQ ID NO: 3, an N-terminus of the sequence of SEQ ID NO: 3 may be further acetylated. Or, in this specific embodiment, a C-terminus of the sequence of SEQ ID NO: 3 may be further amidated. Or, in this specific embodiment, an N-terminus and a C-terminus of the sequence of SEQ ID NO: 3 may be further acetylated and amidated, respectively.

The novel peptide comprising an α-helix peptide and a short peptide of the present disclosure mentioned above may have following effects, but it is not limited thereto.

The novel peptide of the present disclosure mentioned above has antimicrobial activity. "Antimicrobial activity" used in the present disclosure refers to the peptide being capable of changing the function or metabolism of a target microorganism, such as influencing reproduction, growth, toxin production, subsistence, etc. In one embodiment, antimicrobial activity refers to inhibiting microorganism growth. Moreover, in one specific embodiment, antimicrobial activity refers to the peptide being capable of killing at least one kind of microorganism.

Examples of the microorganism mentioned in the present disclosure may comprise a bacterium, a fungus, a virus, a protozoan, etc., especially a microorganism having cell or structure with lipid bilayer, but they are not limited thereto.

The foregoing bacterium may comprise a Gram-positive bacterium and/or a Gram-negative bacterium, but it is not limited thereto. Examples of the Gram-positive bacterium may comprise *Staphylococcus aureus, Staphylococcus epidermidis, Streptococcus agalactiae*, Group A *streptococcus, Streptococcus pyogene*, Group B gram-positive *streptococcus, Listeria monocytogenes*, etc., but they are not limited thereto. Moreover, examples of the Gram-negative bacterium may comprise, but are not limited to, *Escherichia coli, Pseudomonas aeruginosa, Salmonella, Haemophilus* influenza, *Vibrio cholera, Vibrio parahaemolyticus, Helicobacter pylori*, etc.

The preceding fungus may comprise yeast, such as *Candida albicans*. Moreover, the virus mentioned above may comprise, but is not limited to Measles virus, herpes simplex virus (HSV) (such as HSV-1, HSV-2), human immunodeficiency virus (HIV), hepatitis C virus (HCV), vesicular stomatitis virus (VSV), visna virus or cytomegalovirus (CMV). Furthermore, the protozoan mentioned above may comprise giardia, but it is not limited thereto.

In addition, the novel peptide of the present disclosure mentioned above has anticancer activity and has no influence on a normal cell. In other words, the novel peptide of the present disclosure mentioned above has high selectivity to a cancer cell.

"Anticancer activity" used in the present disclosure refers to the peptide being capable of changing the function or metabolism of a target cancer cell, such as influencing reproduction, growth, toxin production, subsistence, etc., but it is not limited thereto. In one embodiment, anticancer activity refers to inhibit cancer cell growth. Moreover, in one specific embodiment, anticancer activity refers to the peptide being capable of killing at least one kind of cancer cell.

The cancer cell mentioned above has no particular limitation, and may be, for example, a lung cancer cell, an oral cancer cell, a prostate cancer cell, a breast cancer cell, a liver cancer cell, a pancreas cancer cell, etc., but it is not limited thereto. Furthermore, the foregoing lung cancer cell may comprise a lung adenocarcinoma cell, but it is not limited thereto. Examples of the foregoing oral cancer cell may comprise, but are not limited to, an oral squamous-cell carcinoma (OSCC) cell.

In addition, the novel peptide of the present disclosure mentioned above further is capable of killing a cancer cell resistant to anticancer drugs. In one embodiment, the novel peptide of the present disclosure mentioned above is capable of killing a lung adenocarcinoma cell resistant to gefitinib.

"Wound-healing" used in the present disclosure may be continuous, dynamic and complicated processes, which may comprise, but are not limited to, cell proliferation, cell migration, etc. In one embodiment, the phrase "wound-healing promoting" used in the present disclosure also may refer to "enhancing cell proliferation" or "enhancing cell migration", but it is not limited thereto.

The novel peptide of the present disclosure can be only used as an antimicrobial peptide, an anticancer peptide, or a wound healing promoting peptide, or it can be used as an antimicrobial, anticancer and wound healing promoting peptide at the same time, depending on demand, and has no particular limitation.

In another embodiment of the present disclosure, the present disclosure provides a pharmaceutical composition which may comprise any novel peptide of the present disclosure mentioned above and a pharmaceutically acceptable carrier or salt.

The preceding pharmaceutical composition of the present disclosure has antimicrobial, anticancer and/or wound-healing promoting activities, and has no influence on a normal cell.

Examples of the microorganism which can be attacked by the pharmaceutical composition of the present disclosure may comprise a bacterium, a fungus, a virus, a protozoan, etc., and especially a microorganism having cell or structure with lipid bilayer, but they are not limited thereto.

The foregoing bacterium may comprise a Gram-positive bacterium and/or a Gram-negative bacterium, but it is not limited thereto. Examples of the Gram-positive bacterium may comprise *Staphylococcus aureus, Staphylococcus epidermidis, Streptococcus agalactiae*, Group A *streptococcus, Streptococcus pyogene*, Group B gram-positive *streptococcus, Listeria monocytogenes*, etc., but they are not limited thereto. Moreover, examples of the Gram-negative bacterium may comprise, but are not limited to, *Escherichia coli, Pseudomonas aeruginosa, Salmonella, Haemophilus influenza, Vibrio cholera, Vibrio parahaemolyticus, Helicobacter pylori*, etc.

The preceding fungus may comprise yeast, such as *Candida albicans*. Moreover, the virus mentioned above may comprise, but is not limited to, the Measles virus, herpes simplex virus (HSV) (such as HSV-1, HSV-2), human immunodeficiency virus (HIV), hepatitis C virus (HCV), vesicular stomatitis virus (VSV), visna virus or cytomegalovirus (CMV). Furthermore, the protozoan mentioned above may comprise giardia, but it is not limited thereto.

The cancer cell mentioned above has no particular limitation, and may be, for example, a lung cancer cell, an oral cancer cell, a prostate cancer cell, a breast cancer cell, a liver cancer cell, a pancreas cancer cell, etc., but it is not limited thereto. Furthermore, the foregoing lung cancer cell may comprise a lung adenocarcinoma cell, but it is not limited thereto. Examples of the foregoing oral cancer cell may comprise an oral squamous-cell carcinoma (OSCC) cell, but they are not limited thereto.

In addition, the preceding pharmaceutical composition of the present disclosure is capable of killing a cancer cell resistant to anticancer drugs. In one embodiment, the novel peptide of the present disclosure mentioned above is capable of killing a lung adenocarcinoma cell resistant to gefitinib.

The effect of wound-healing promoting of the pharmaceutical composition of the present disclosure also can refer to effect of "enhancing cell proliferation", "enhancing cell migration", etc., but is not limited thereto.

In the preceding pharmaceutical composition of the present disclosure, the pharmaceutically acceptable carrier mentioned above may comprise, but is not limited to, a solvent, a dispersion medium, a coating, an antibacterial and antifungal agent, or an isotonic and absorption delaying agent, etc. which is compatible to pharmaceutical administration. The pharmaceutical composition can be formulated into dosage forms for different administration routes utilizing conventional methods.

Moreover, the pharmaceutically acceptable salt mentioned above may comprise, but is not limited to, inorganic cation salt, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also comprise organic salt, such as dicyclohexylamine salt, methyl-D-glucamine, and amino acid salt such as arginine, lysine, histidine, or glutamine.

The pharmaceutical composition of the present disclosure may be administered orally, parenterally by an inhalation spray, or via an implanted reservoir. The parenteral methods may comprise subcutaneous, intracutaneous, intravenous, intramuscular, intra-articular, intra-arterial, intrasynovial, intrasternal, intrathecal, and intraleaional, as well as infusion techniques.

An oral composition can comprise, but is not limited to, tablets, capsules, emulsions, and aqueous suspensions, dispersions and solutions.

The pharmaceutical composition of the present disclosure may be administered to a plant or an animal, etc. The preceding animal may be a fish, a bird, a mammal, etc., but it is not limited thereto. Examples of the mammal may include, but is not limited to, a cat, a dog, a bovine, a horse, a pig, a human, etc. In one embodiment, the pharmaceutical composition of the present disclosure may be administered to a human.

In another embodiment of the present disclosure, the present disclosure provides a method for preparing a pharmaceutical composition with antimicrobial, anticancer and/or wound-healing promoting activities. The method for preparing a pharmaceutical composition with antimicrobial, anticancer and/or wound-healing promoting activities may comprise the following step, but it is not limited thereto.

In one embodiment, an effective amount of any novel peptide of the present disclosure mentioned above may be provided, serving as an active ingredient, in preparation of a pharmaceutical composition with antimicrobial, anticancer and/or wound-healing promoting activities, wherein the pharmaceutical composition is capable of inhibiting a microorganism, inhibiting a cancer cell, and/or promoting wound-healing.

In other embodiment, in addition to an effective amount of any novel peptide of the present disclosure mentioned above, a pharmaceutically acceptable carrier or salt may be further provided in preparation of a pharmaceutical composition with antimicrobial, anticancer and/or wound-healing promoting activities.

In another embodiment of the present disclosure, the present disclosure provides a method for inhibiting a microorganism, inhibiting a cancer cell, and/or promoting wound-healing. The method for inhibiting a microorganism, inhibiting a cancer cell, and/or promoting wound-healing may comprise, but is not limited to, providing any one of the pharmaceutical compositions of the present disclosure mentioned above may be administered to a subject in need thereof.

The foregoing subject may comprise a plant or an animal, etc. The animal mentioned above may be a fish, a bird, a mammal, etc., but it is not limited thereto. Examples of the mammal may comprise, but is not limited to a cat, a dog, a bovine, a horse, a pig, a human, etc. In one embodiment, the foregoing subject is a human.

EXAMPLES

A. Materials and Methods

1. Ethics Statement

Human venous blood was collected from three healthy volunteers with prior written informed consent and approval from the Institution Review Broad of the National Taiwan University Hospital Hsin-chu Branch.

All animal experiments were performed in accordance with the animal guidelines of the National Tsing Hua University Institutional Animal Care and Use Committee (Permit Number: 10260). All nude mice were sacrificed under $CO_2$, and all efforts were made to minimize suffering.

2. Peptide Preparation

The designed peptides were synthesized. The identity of the peptides was checked by electrospray mass spectroscopy and the purity (>95%) was assessed by HPLC. Peptide concentration was determined by using the UV/Visible spectrophotometer at 280 nm. Buffers were prepared in double glass-distilled water.

3. Bacteria Culture

*Escherichia coli* strain (ATCC 25922), *Staphylococcus aureus* subsp strain (ATCC 25923, methicillin-resistant), and *Pseudomonas aeruginosa* Migula strain (ATCC 27853, ampicillin-resistant) were used to test the antibacterial activity of the peptides. Bacteria were cultured in sterilized Mueller-Hinton (MH) culturing medium at 200 rpm and 37° C. for 8 hours.

After 8 hours culture, concentration of the inoculums were determined by measuring absorbance of optical density at 600 nm (OD 600=1, equal to approximately $10^8$ CFU/mL) with UV/Visible spectrophotometer.

4. Antimicrobial Activity

The antibacterial activities were determined by the standard broth microdilution method of National Committee for Clinical Laboratory Standards with the LYM broth. The LYM broth contains 5.4 mM KCl, 5.6 mM $Na_2HPO_4$, 0.5 mM $MgSO_4$, and 1.0 mM sodium citrate. In addition, 0.4 mg of $ZnCl_2$, 2.0 mg of $FeCl_3 \cdot 6H_2O$, 0.1 mg of $CuSO_4 \cdot 5H_2O$, 0.1 mg of $MnSO_4 \cdot H_2O$, 0.1 mg of $Na_2B_4O_7 \cdot 10H_2O$, 700 mg of amino acid mixtures without tryptophan (Clontech), and 20 mg of L-Tryptophan were added per liter of medium. A vitamin mixture (100×, Sigma) and glucose at final concentration of 2% were also added.

1 µl peptide solutions (ranging from 5000 µg/ml to 78 µg/ml in serial dilution) was prepared and mixed with 99 µl inoculum ($5 \times 10^5$ CFU/ml) in polypropylene 96-well plate. The turbidity at OD 600 nm was measured by ELISA plate reader (Thermo Max, Molecular Devices, Sunnyvale, Calif.). The absorbance of culture medium and inoculum suspension without peptides were used as the negative and positive control, respectively. The minimum inhibitory concentration (MIC) value is the lowest concentration of peptide at which there is no obvious growth (equal or more than 90%). MICs were converted to a color scale and displayed using the TreeView Program (Arnusch C J, Ulm H, Josten M, Shadkchan Y, Osherov N, et al. (2012) Ultrashort Peptide Bioconjugates Are Exclusively Antifungal Agents and Synergize with Cyclodextrin and Amphotericin B. Antimcrob Agents Chemother 56: 1-9.; Eisen M B, Spellman P T, Brown P O and Botstein D (1998) Cluster analysis and display of genome-wide expression patterns. Proc Natl Acad Sci 95: 14863-14868.). All peptides were tested in triplicate.

5. Hemolytic Activity

Human venous blood was collected by a venous blood collection tube (BD Vacutainer, REF 367525). Serum was removed by PBS buffer washing and centrifugation at 800 g for 5 minutes. The above processes were repeated at least three times to remove the serum completely.

50 µl of peptides (ranging 1.6 mM to 3.1 µM in serial dilution) mixed with 50 µl of 10% hRBC and incubated at 37° C. for 1 hour. The supernatant were collected after centrifugation at 800 g for 5 minutes. The amount of hemoglobin released from hRBC was determined by measuring the absorbance at 405 nm. 10% hRBC without peptide and treated with 1% Triton X-100 represented negative and positive control, respectively.

6. Cell Culture

Human lung cancer line PC9 and A549, oral squamous cell carcinoma cell line OECM-1 were cultured in RPMI medium supplemented with 10% fetal bovine serum and antibiotic. Human tongue carcinoma cell line SAS, oral cancer cell line C9, and human diploid fibroblast (HFW) were cultured in DMEM medium supplemented with 10% fetal bovine serum and antibiotic. Cells were cultured in a humidified incubator containing 5% $CO_2$ at 37° C.

PC9 and the gefitinib resistant PC9 strain (PC9-G) were received from Dr. Yu-Ting Chou, Institute of Biotechnology, National Tsing Hua University. PC9-G was generated from culturing PC9 cells in gefitinib (500 nM) for 60 days.

7. Cell Toxicity

The MTT assay was employed to determine the in vitro cytotoxicity. All cancer cell lines were seeded in 96-well plate with concentration 5000 cells/100 µl/well and incubated for 24 hours. HFW was seeded with 8000 cells/100 µl/well.

After medium was removed, 100 µl fresh medium containing peptide (ranging from 50 µM to 3.13 µM, HFW was treated with 75 µM and 100 µM peptide additionally) was added to the wells. Following 3, 12 or 24 hour incubation, fresh medium with MTT (0.5 mg/ml) was replaced and incubated for 3 hours. After medium/MTT was removed, DMSO was added at 100 µl for dissolving the formazan crystal. Cell survival rate was calculated by measuring the absorbance at 540 nm using Multi-labeled Microplate Reader (VICTOR3). For cancer cells, medium mixed with H₂O₂ (aq) represented positive control (all cells died) while medium only represented negative control. For normal cells, medium only represented positive control (all cells lived) while medium mixed with H₂O₂ (aq) represented negative control (all cells died).

8. Cell Live Image

PC9 and HFW cells (~10⁵ cells) were pre-seeded in 6-cm polystyrene dishes for 24 hours. Cell nuclear is labeled by 4',6-diamidino-2-phenylindole (DAPI) with a final concentration of 10 μg/ml. After 10 minutes of incubation, the cells were washed by PBS. FITC-K4R2Nal2S1-NH2 was added to the dishes with the final concentration of 12 μM. After incubation for 5, 10, 20 minutes or 1 hour at 37° C., the cells were washed with PBS. The images of FITC-K4R2Nal2S1-NH₂ in PC9 cells and HFW cells were observed using the Inverted Fluorescent Microscope Zeiss/Observer.Z1.

9. Western Blotting

PC9 cells were seeded in 10-cm polystyrene dishes for 48 hours. About seventy percent full of cells were treated with 12 μM K4R2Nal2S1 for 10 minutes, 1 hour or 24 hours. RPMI medium without peptide treated for 24 hours which was used as negative control.

Cells were collected by 200 μl RIPA and protease inhibitor blended buffer. After sonication and centrifugation for 10 minutes, 13000 rpm at 4° C., supernatants (lysis of cell) were collected. Protein concentrations of cell extracts were determined by Bradford reagent. Equal amount of boiled lysates (total 50 μg) were separated on 10% acrylamide gel. The gel was transferred to PVDF membrane in electro-blot system, 300 V, 350 A, and 80 minutes.

The membrane was incubated in blocking buffer (5% skim milk, TBST buffer) for 1 hour at room temperature and washed in TBST buffer twice. Blocked membrane was incubated with Caspase-3 antibody (EPITOMICS, clone ID: E83-77) overnight at 4° C., washed for five times, and then incubated in secondary antibody (HRP, GeneTex catalogue number: GTX21311-01) for 1 hour at room temperature. The signals were visualized by enhanced chemiluminescence (ECL) and recorded by a detected system (ImageQuant LAS 4000 mini).

10. Mice and Pathological Studies 12 male nude mice (BALB/cAnN.Cg-Foxn1nu/CrlNarl) were purchased from National Laboratory Animal Center, Taiwan.

100 μl human lung cancer cell PC9 (3×10⁶ cells) in Matrigel (Corning) was injected subcutaneously into the dorsal side of 5-week-old male nude mice. Each mouse was inoculated two sites on its back (Taguchi F, Koh Y, Koizumi F, Tamura T, Saijo N, et al. (2004) Anticancer effects of ZD6474, a VEGF receptor tyrosine kinase inhibitor, in gefitinib ("Iressa")-sensitive and resistant xenograft models. Cancer Sci 95: 984-989.). 1 week 5 days after implantation (cancer size>95 mm³), 12 mice were allocated randomly into two group. One group was received K4R2Nal2S1 (5 mg/Kg, dissolving in 100 μl PBS buffer) by tail vein injection three times a week, the other group was injected PBS as control.

Body weight and cancer size were measured three times a week. The cancer volume was calculated by formula of width²×length×0.52. The cancer volume below 100% of the pretreatment volume was defined as "cancer reduction" (Taguchi F, Koh Y, Koizumi F, Tamura T, Saijo N, et al. (2004) Anticancer effects of ZD6474, a VEGF receptor tyrosine kinase inhibitor, in gefitinib ("Iressa")-sensitive and resistant xenograft models. Cancer Sci 95: 984-989.). "Cancer reduction" was confirmed when the mice were dissected.

The mice were sacrificed after treatment of 40 days, the cancers were removed, photographed, and weighed. All animal experiments were performed in accordance with the animal guidelines of the National Tsing Hua University Institutional Animal Care and approved by Animal Care Committee.

Solid cancers were fixed in 4% formaldehyde buffer. Paraffin-embedded tissues were cut to 2 μm-thickness sections, and deparaffinized in ultraclear buffer (J.T. Baker) and graded ethanol. The morphology of cancers was obtained by Hematoxylin and eosin (H&E) stained sections. In addition, the sections were immunostained with anti-cleaved-PARP (1:100) antibody (Cell Signaling, clone number: D65E10).

Tissue images were captured using light microscope (Eclipse E400, Nikon) with digital microscopy camera (AxioCam ICc 5, ZEISS), at 40×, 200× and 400× fields.

Results

1. Peptide Design

Previously, the inventors had developed a strategy to boost salt resistance and serum stability of short antimicrobial peptides by adding β-naphthylalanine to their termini (Chu H L, Yu H Y, Yip B S, Chih Y H, Liang C W, et al. (2013) Boosting salt resistance of short antimicrobial peptides. Antimicrob. Agents Chemother. 57: 4050-4052.). This strategy has been applied successfully to 51 peptide (SEQ ID NO: 4) and the ultrashort peptide KWWK (SEQ ID NO: 5).

However, peptides with β-naphthylalanine end-tags also demonstrate higher cell lytic activity (cytotoxicity) (Chu H L, Yu H Y, Yip B S, Chih Y H, Liang C W, et al. (2013) Boosting salt resistance of short antimicrobial peptides. Antimicrob. Agents Chemother. 57: 4050-4052.). This problem may be compensated by adding positive charge residues to N- and/or C-terminus of the antimicrobial peptides (Yin L M, Edwards M A, Li J, Yip C M and Deber C M (2012) Roles of Hydrophobicity and Charge Distribution of Cationic Antimicrobial Peptides in Peptide-Membrane Interactions. J Biol Chem 287: 7738-7745.).

Herein, Nal2-S1, K4R2-Nal2-S1, and K6-Nal2-S1 peptides were designed and synthesized and compared their antimicrobial and anticancer activities as well as their cytotoxicities with the parent peptide 51. The sequences and molecular weights of S1, Nal2S1, K4R2-Nal2-S1, and K6-Nal2-S1 are listed in following Table 1.

TABLE 1

Primary structure of S1 and its analogues

| Peptide | Sequence[a] | Molecular weight |
|---|---|---|
| S1 | Ac-KKWRKWLAKK-NH₂ (SEQ ID NO: 4) | 1412.79 |
| Nal2-S1 | Ac-Nal-Nal-KKWRKWLAKK-NH₂ (SEQ ID NO: 1) | 1807.2 |
| K4R2-Nal2-S1 | Ac-KKKKRR-Nal-Nal-KKWRKWLAKK-NH₂ (SEQ ID NO: 2) | 2631.58 |
| K6-Nal2-S1 | Ac-KKKKKK-Nal-Nal-KKWRKWLAKK-NH₂ (SEQ ID NO: 3) | 2576.26 |

[a]β-naphthylalanine (Nal)

2. Antimicrobial Activity

The activities of S1 peptide and its analogs were tested against Gram-positive and Gram-negative bacterium under several salt concentrations.

The minimum inhibitory concentrations of the peptides were analyzed, and the results are shown in Table 2. Table 2 shows that all three peptides, S1. Nal2-S1 and K4R2-Nal2-S1, are very effective against bacterium in LYM broth condition.

TABLE 2

Minimum inhibitory concentrations (MICs) of Ampicillin (AP), S1,
Nal2-S1, K4R2-Nal2-S1, K6-Nal2-S1 peptides to *Escherichia coli*,
*Staphylococcus aureus*, and *Pseudomonas aeruginosa*
under different concentrations of NaCl.

| | | | LYM | | | | | | | | | | | | | | |
|---|---|---|---|---|---|---|---|---|---|---|---|---|---|---|---|---|---|
| | | | control | | | NaCl | | | | | | | | | | | |
| | | | | | | 50 mM | | | | 100 mM | | | | 200 mM | | | |
| Species | AP | S1 | Nal2-S1 | K4R2-Nal2-S1 | K6-Nal2-S1 | S1 | Nal2-S1 | K4R2-Nal2-S1 | K6-Nal2-S1 | S1 | Nal2-S1 | K4R2-Nal2-S1 | K6-Nal2-S1 | S1 | Nal2-S1 | K4R2-Nal2-S1 | K6-Nal2-S1 |
| *E. coli* ATCC 25922 | 25 | 6.25 | 3.1 | 3.1 | 6.25 | 12.5 | 3.1 | 6.25 | 6.25 | 12.5 | 6.25 | 6.25 | 12.5 | >50 | 6.25 | 6.25 | 12.5 |
| *S. aureus* ATCC 25923 | 3.1 | 3.1 | 3.1 | 3.1 | 1.6 | 25 | 3.1 | 3.1 | 3.1 | 50 | 3.1 | 6.25 | 12.5 | >50 | 3.1 | 6.25 | 25 |
| *P. arugenosa* ATCC 27853 | N.D. | 3.1 | 1.6 | 3.1 | 3.1 | 25 | 3.1 | 3.1 | 6.25 | >50 | 3.1 | 3.1 | 6.25 | >50 | 6.25 | 6.25 | 25 |

*MIC (μg mL−1), Minimal Inhibition Concentration. AP: Ampicillin. N.D: Ampicillin-resistant.

Nal2-S1 and K4R2-Nal2-S1 demonstrate promising activities in high-salt conditions. However, the activities of K6-Nal2-S1 are diminished by the addition of 100 or 200 mM NaCl.

3. Cytotoxicity

The cytotoxicities of S1 and its analogs on human lung cancer cells (i.e, PC9, PC9-G and A549), human oral cancer cells (i.e, C9, OECM-1, and SAS), and human fibroblast (HFW) were evaluated by MTT assay for 3, 12 and 24 hours.

Figure 1B:
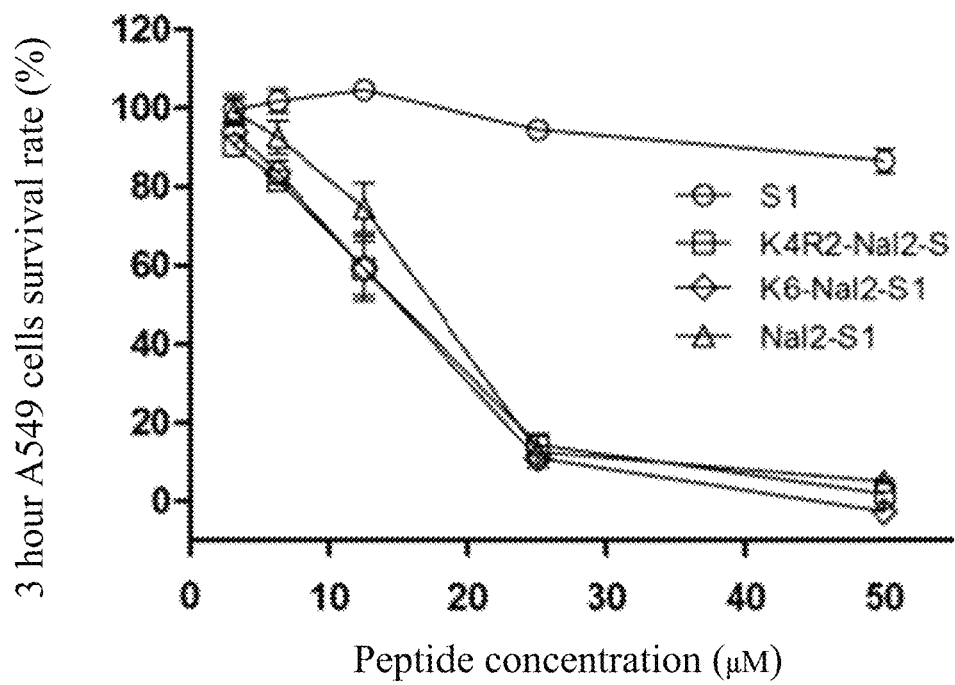
FIG. 1B shows cell survival rates of A549 and OECM-1 cells after being treated with S1, Nal2-S1, K4R2-Nal2-S1 and K6-Nal2-S1 peptides for 3 hours (the activities of S1, Nal2-S1, K4R2-Nal2-S1 and K6-Nal2-S1 against A549 and OECM-1 cell lines)
Figure 1B:
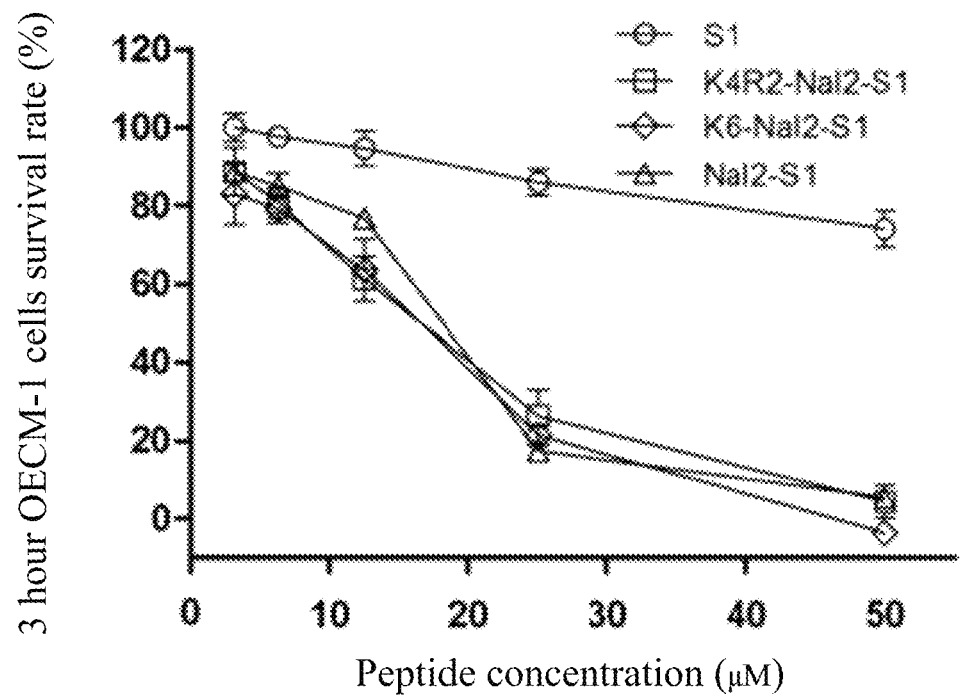
Figure 1C:
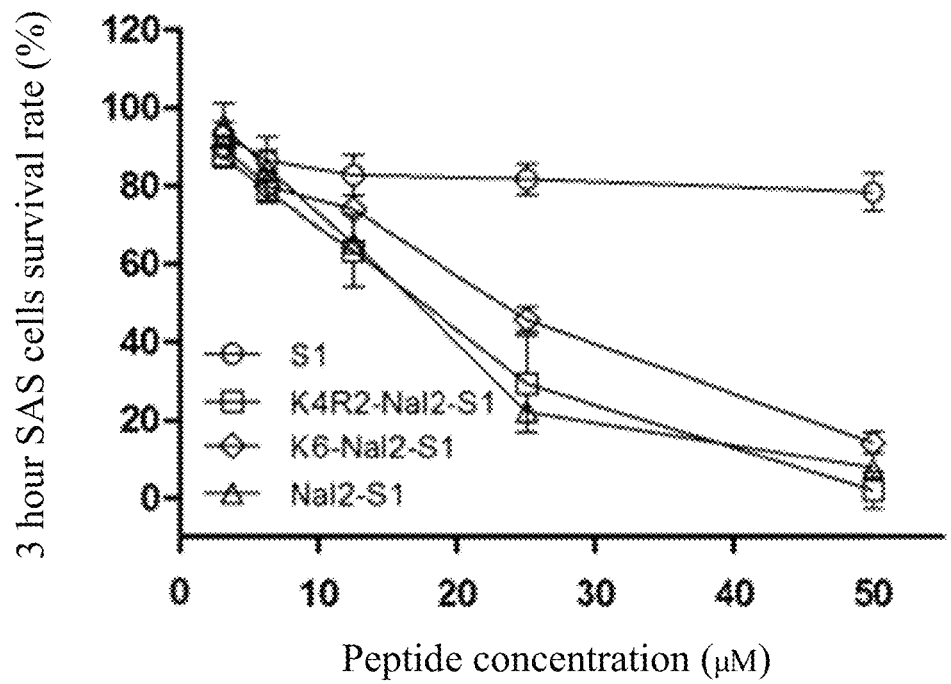
FIG. 1C shows cell survival rates of SAS and C9 cells after being treated with S1, Nal2-S1, K4R2-Nal2-S1 and K6-Nal2-S1 peptides for 3 hours (the activities of S1, Nal2-S1, K4R2-Nal2-S1 and K6-Nal2-S1 against SAS and C9 cell lines)
Figure 1C:
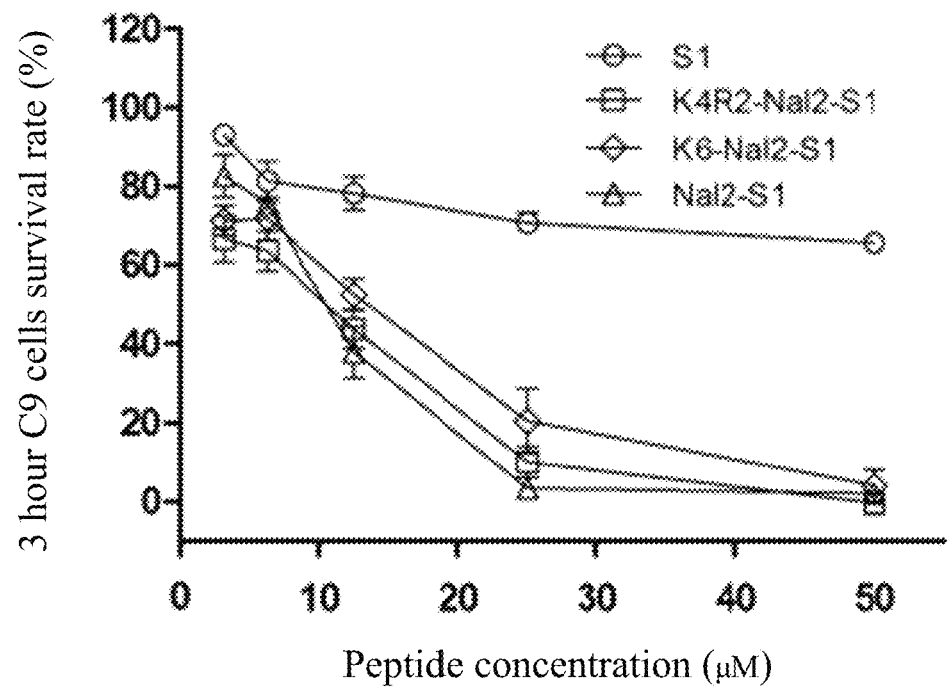
Figure 2A:
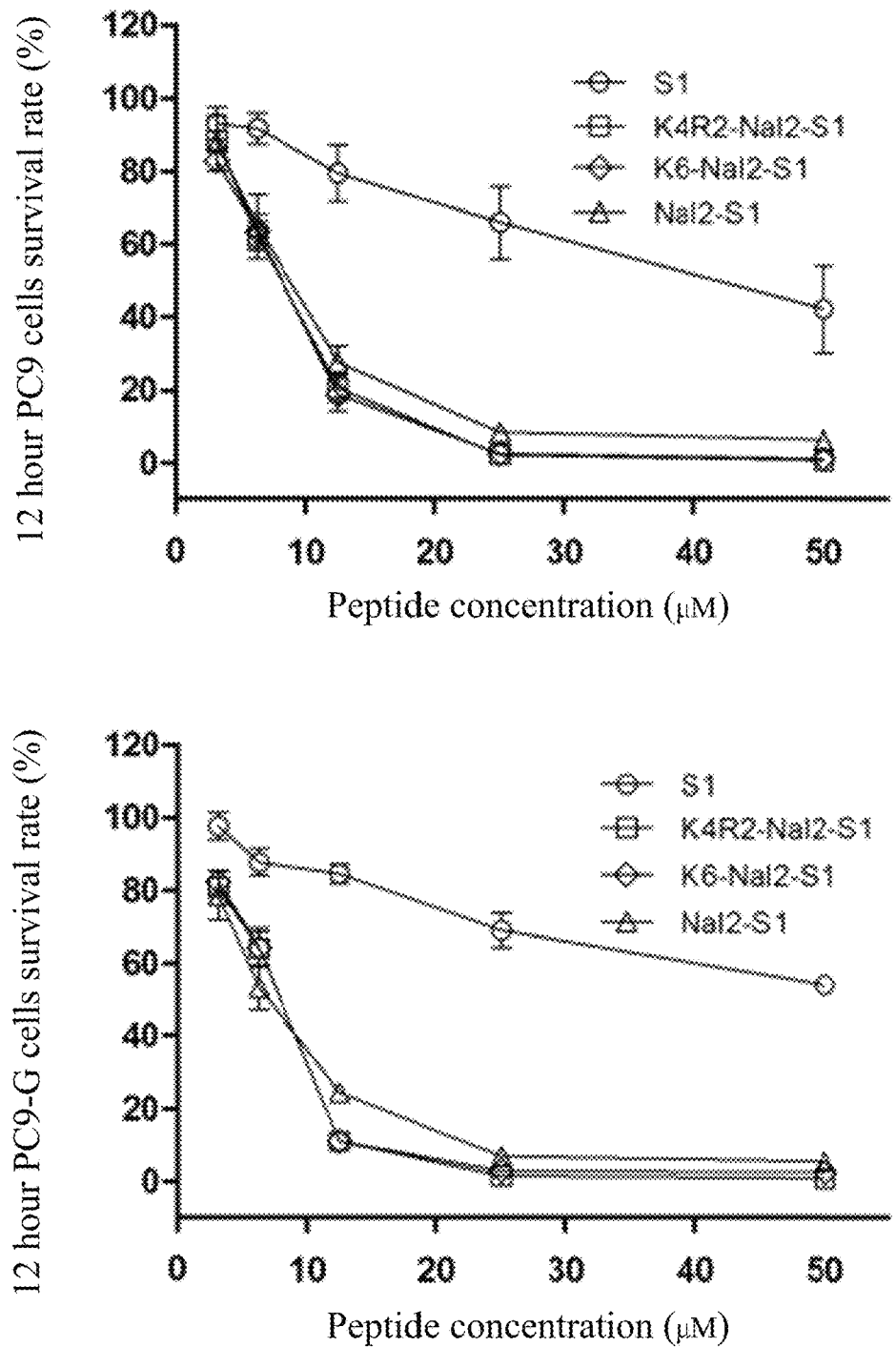
FIG. 2A shows cell survival rates of PC9 and PC9-G cells after being treated with S1, Nal2-S1, K4R2-Nal2-S1 and K6-Nal2-S1 peptides for 12 hours (the activities of S1, Nal2-S1, K4R2-Nal2-S1 and K6-Nal2-S1 against PC9 and PC9-G cell lines)
Figure 2B:
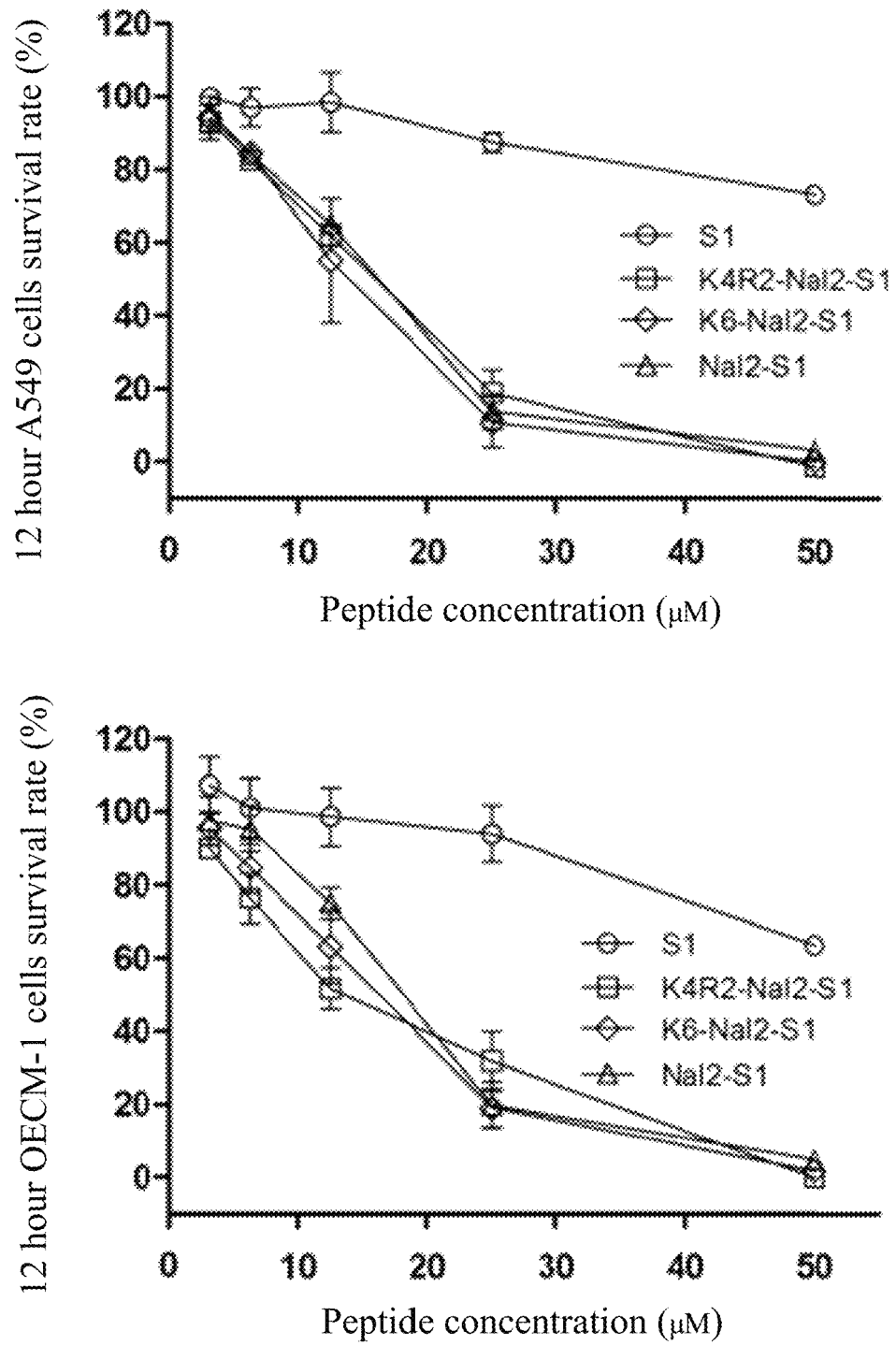
FIG. 2B shows cell survival rates of A549 and OECM-1 cells after being treated with S1, Nal2-S1, K4R2-Nal2-S1 and K6-Nal2-S1 peptides for 12 hours (the activities of S1, Nal2-S1, K4R2-Nal2-S1 and K6-Nal2-S1 against A549 and OECM-1 cell lines)
Figure 2C:
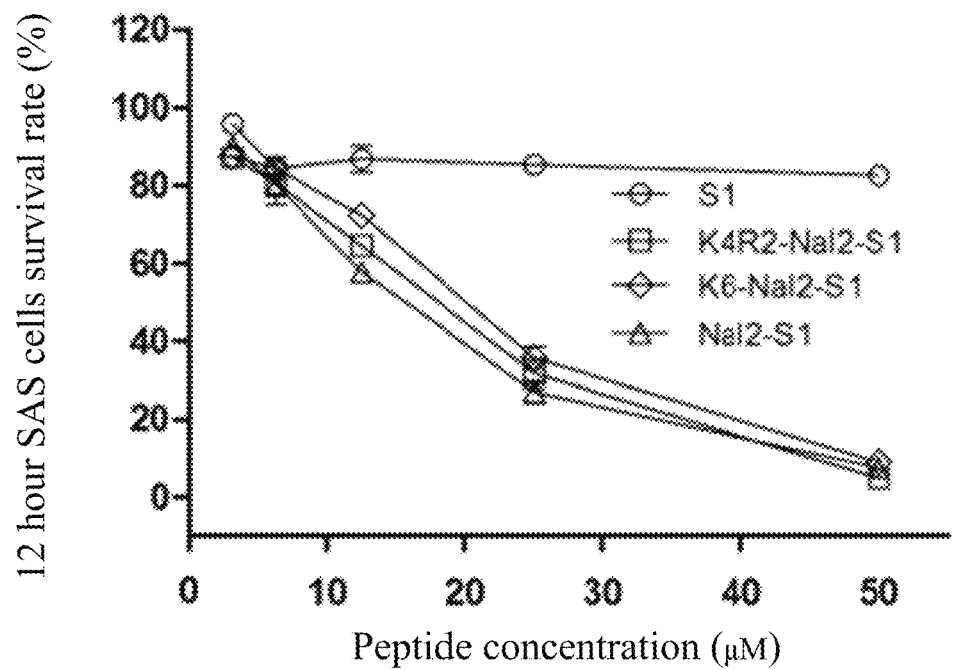
FIG. 2C shows cell survival rates of SAS and C9 cells after being treated with S1, Nal2-S1, K4R2-Nal2-S1 and K6-Nal2-S1 peptides for 12 hours (the activities of S1, Nal2-S1, K4R2-Nal2-S1 and K6-Nal2-S1 against SAS and C9 cell lines)
Figure 2C:
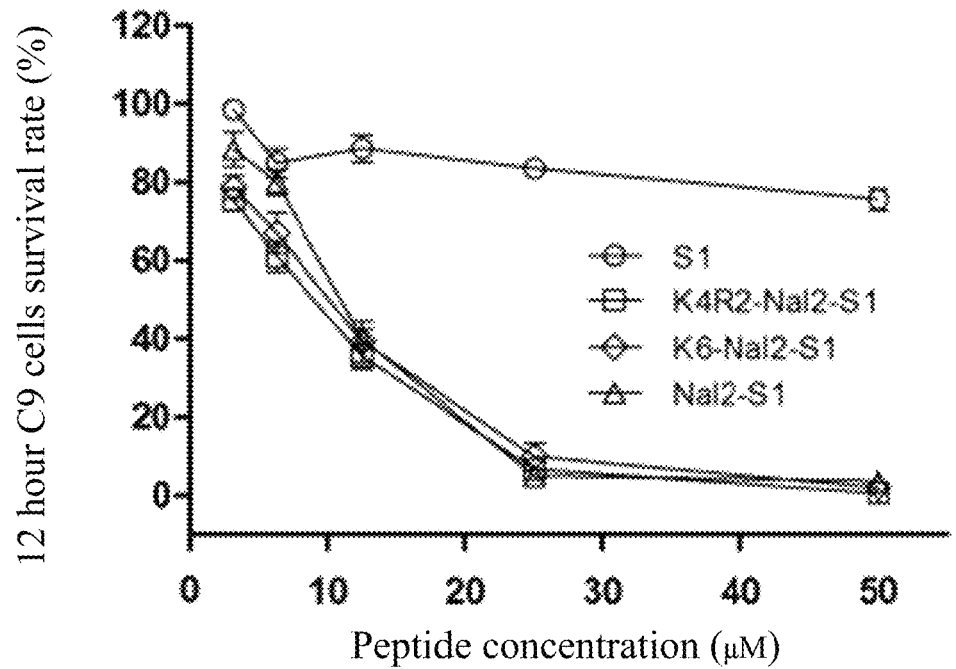
Figure 3A:
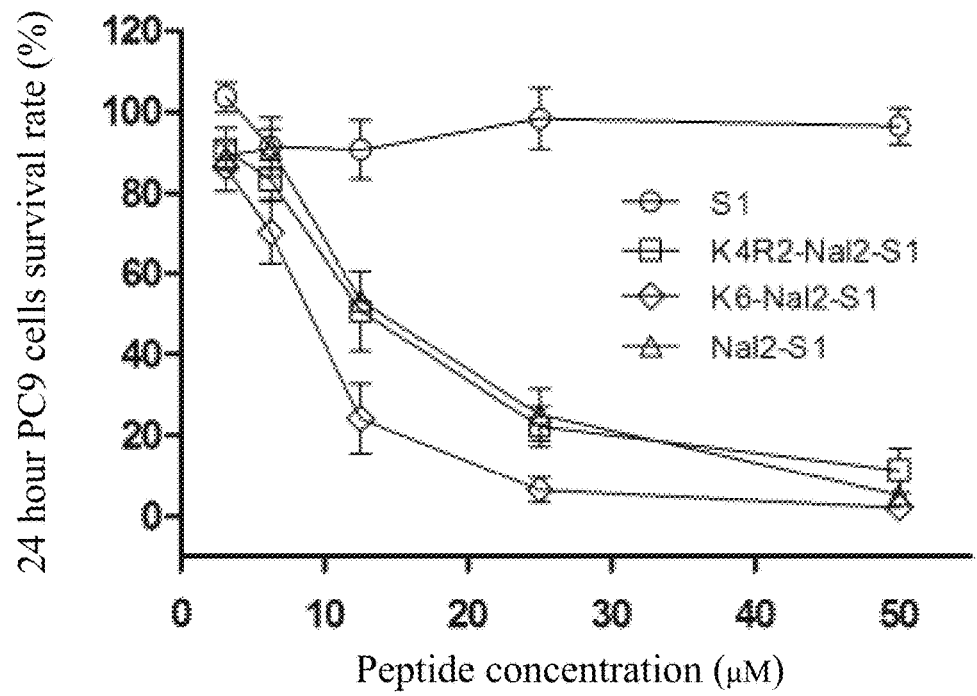
FIG. 3A shows cell survival rates of PC9 and PC9-G cells after being treated with S1, Nal2-S1, K4R2-Nal2-S1 and K6-Nal2-S1 peptides for 24 hours (the activities of S1, Nal2-S1, K4R2-Nal2-S1 and K6-Nal2-S1 against PC9 and PC9-G cell lines)
Figure 3A:
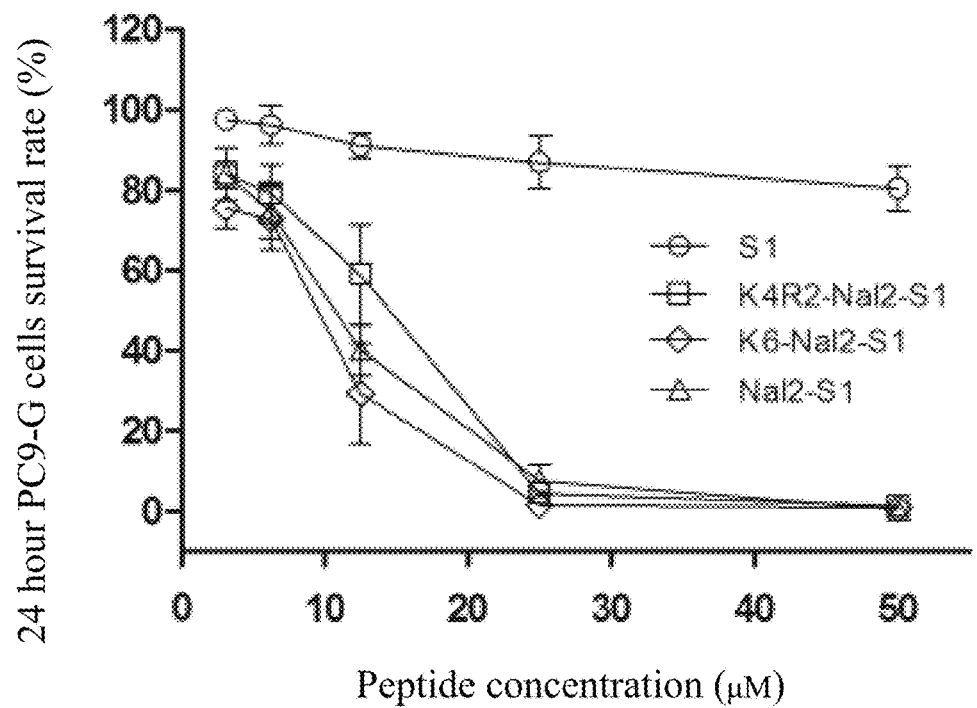
Figure 3B:
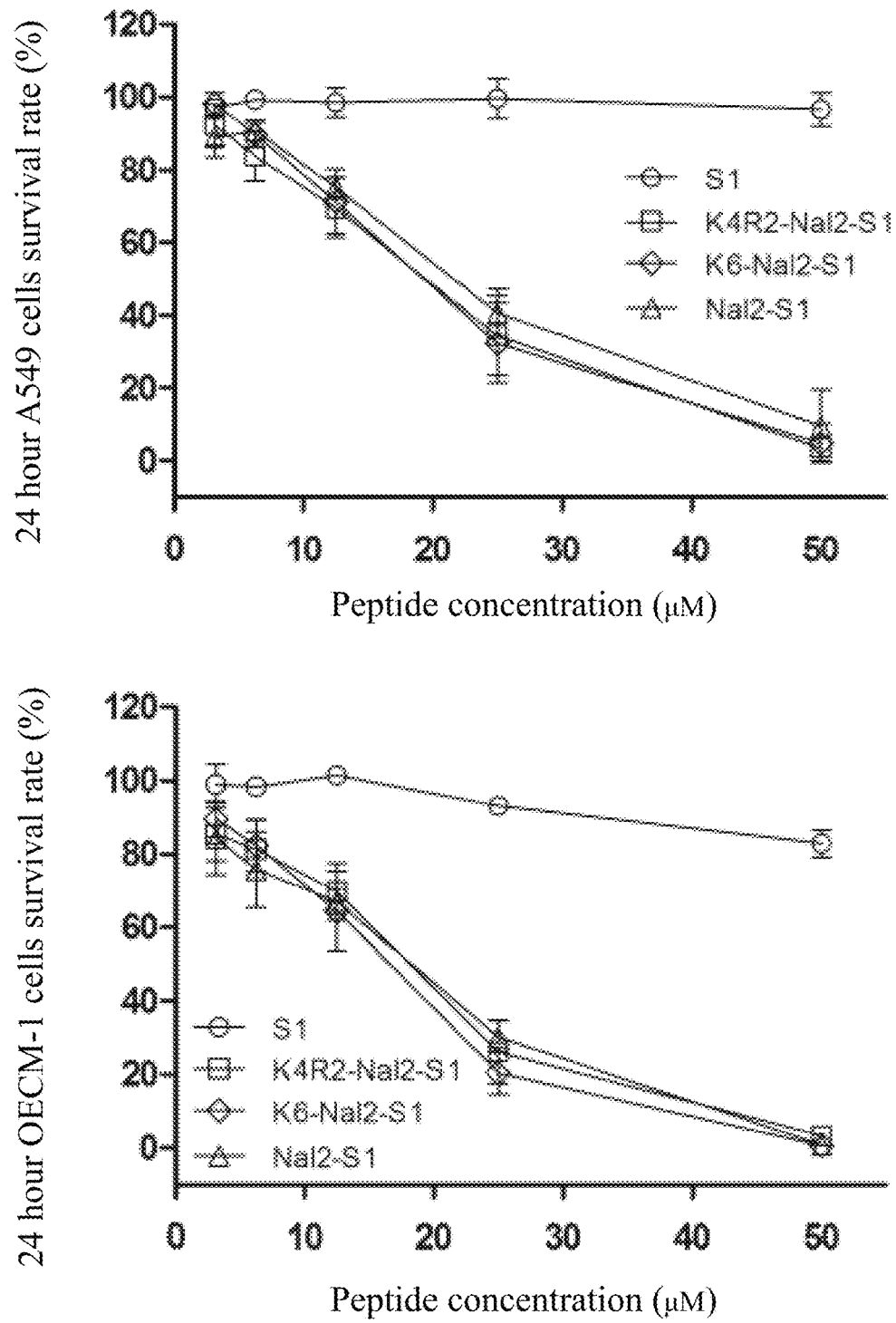
FIG. 3B shows cell survival rates of A549 and OECM-1 cells after being treated with S1, Nal2-S1, K4R2-Nal2-S1 and K6-Nal2-S1 peptides for 24 hours (the activities of S1, Nal2-S1, K4R2-Nal2-S1 and K6-Nal2-S1 against A549 and OECM-1 cell lines)
Figure 3C:
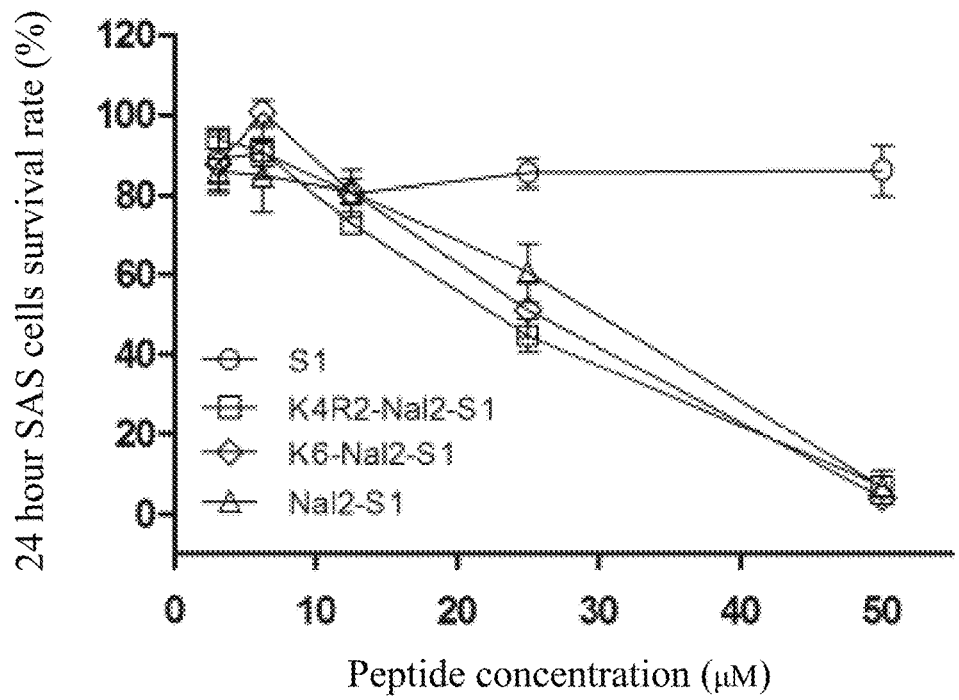
FIG. 3C shows cell survival rates of SAS and C9 cells after being treated with S1, Nal2-S1, K4R2-Nal2-S1 and K6-Nal2-S1 peptides for 24 hours (the activities of S1, Nal2-S1, K4R2-Nal2-S1 and K6-Nal2-S1 against SAS and C9 cell lines)
Figure 3C:
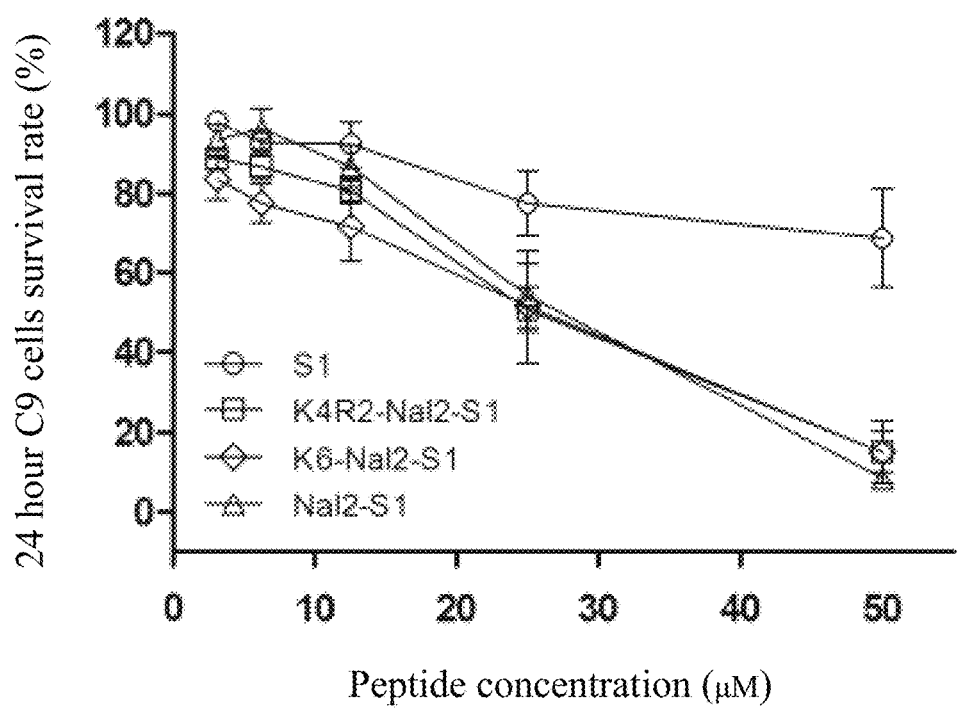

The cytotoxicities of foregoing peptides to the various cancer cells for 3 hours are shown in FIGS. 1A-1C, the cytotoxicities of foregoing peptides to various cancer cells for 12 hours are shown in FIGS. 2A-2C, and the cytotoxicities of foregoing peptides to various cancer cells for 24 hours are shown in FIGS. 3A-3C.

The data showed that after treating the various cancer cells with the peptides for 24 hours, the three β-naphthyl-alanine (Nal) embedded peptides all have potent anticancer activities against different cancer cell lines (see FIGS. 3A-3C).

Similar results were observed at earlier time points (i.e. 3 hours and 12 hours, see FIGS. 1A-1C and FIGS. 2A-2C, respectively).

Figure 4A:
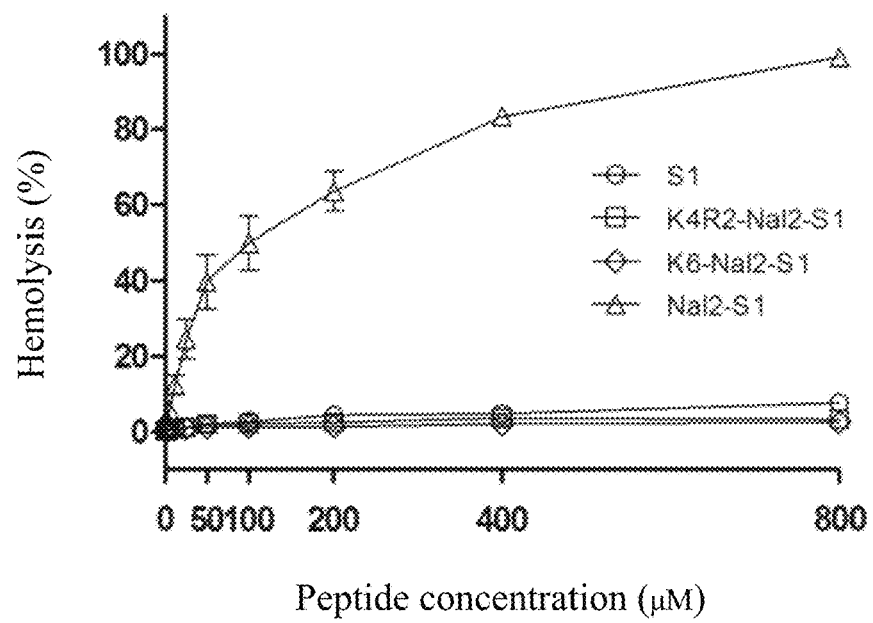
FIG. 4A shows hemolysis to human red blood cells (hRBCs) of S1, Nal2-S1, K4R2-Nal2-S1, and K6-Nal2-S1 peptides.
Figure 4B:
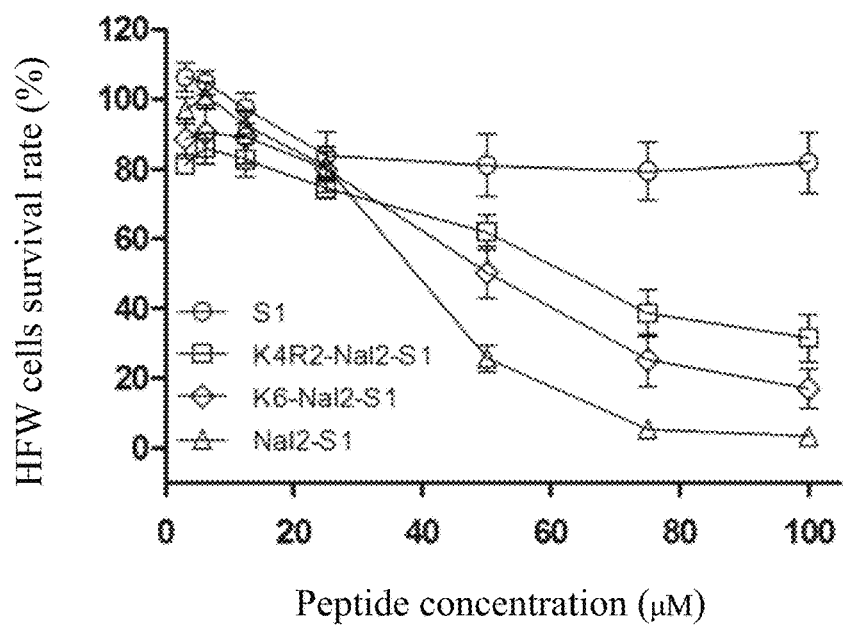
FIG. 4B shows cytotoxicity to human fibroblast (HFW) cells of S1, Nal2-S1, K4R2-Nal2-S1, and K6-Nal2-S1 peptides.

The selectivity of the peptides was investigated using human red blood cells (hRBCs) and human fibroblast (HFW). The results are shown in FIGS. 4A and 4B.

The lytic activity of all peptides toward hRBCs was tested at 37° C. for 1 hour incubation and calculated by minimal hemolytic concentration.

Nal2-S1 peptide displayed 10% hemolytic activity at 25 μM peptide concentration. Surprisingly, the hemolytic activities of K4R2-Nal2-S1 and K6-Nal2-S1 peptides were not found even at 800 μM. The degrees of cytotoxicities of these peptides to HFW were found to be S1 peptide<K4R2-Nal2-S1 peptide<K6-Nal2-S1 peptide<Nal2-S1 peptide.

As K4R2-Nal2-S1 peptide displayed better salt resistance and less toxic to hRBCs and human fibroblast than Nal2-S1 and K6-Nal2-S1 peptides, K4R2-Nal2-S1 peptide was selected to investigate its anticancer activities in PC9 cancer cell line and xenograft animal model.

4. In Vitro Anticancer Mechanism

To investigate the mode of actions of K4R2Nal2-S1 peptide on human cancer cell line (PC9) and human fibroblast (HFW), cells were treated with FITC-labeled K4R2-Nal2-S1. Nucleus was labeled with DAPI, and the blue signal was observed by UV exciting light. The fluorescence distribution of FITC-labeled K4R2-Nal2-S1 peptide on cell membrane was visualized by the inverted fluorescent microscope.

Figure 5A:
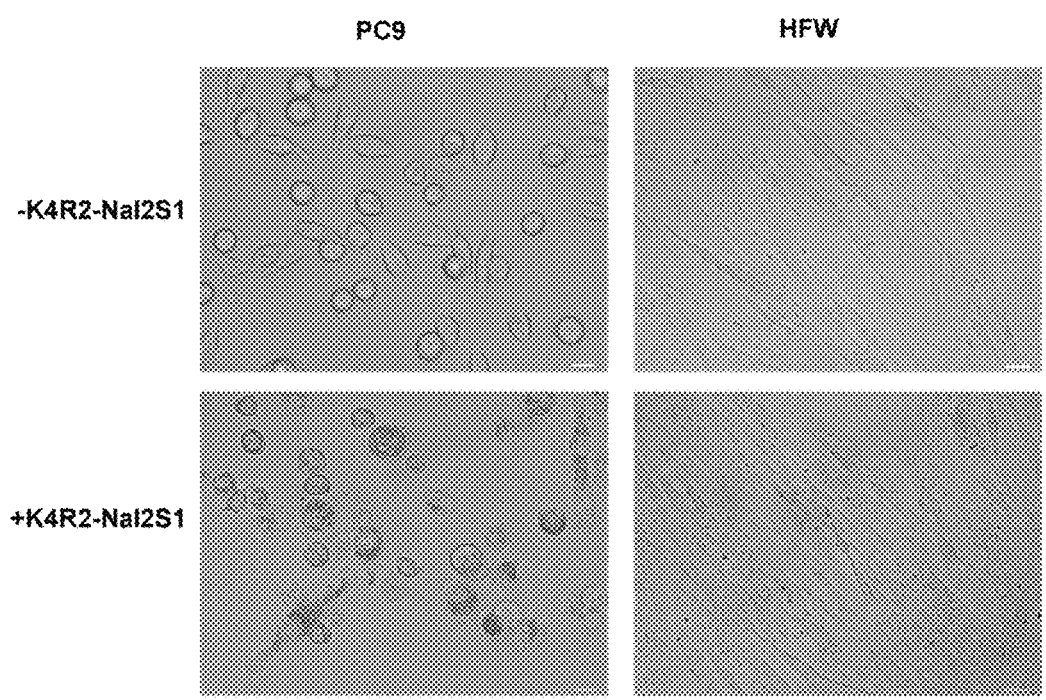
FIG. 5A shows representative phase-contrast images of PC9 and HFW cells treated with or without 12 μM FITC-K4R2-Nal2-S1 peptide for 5 minutes.
Figure 5B:
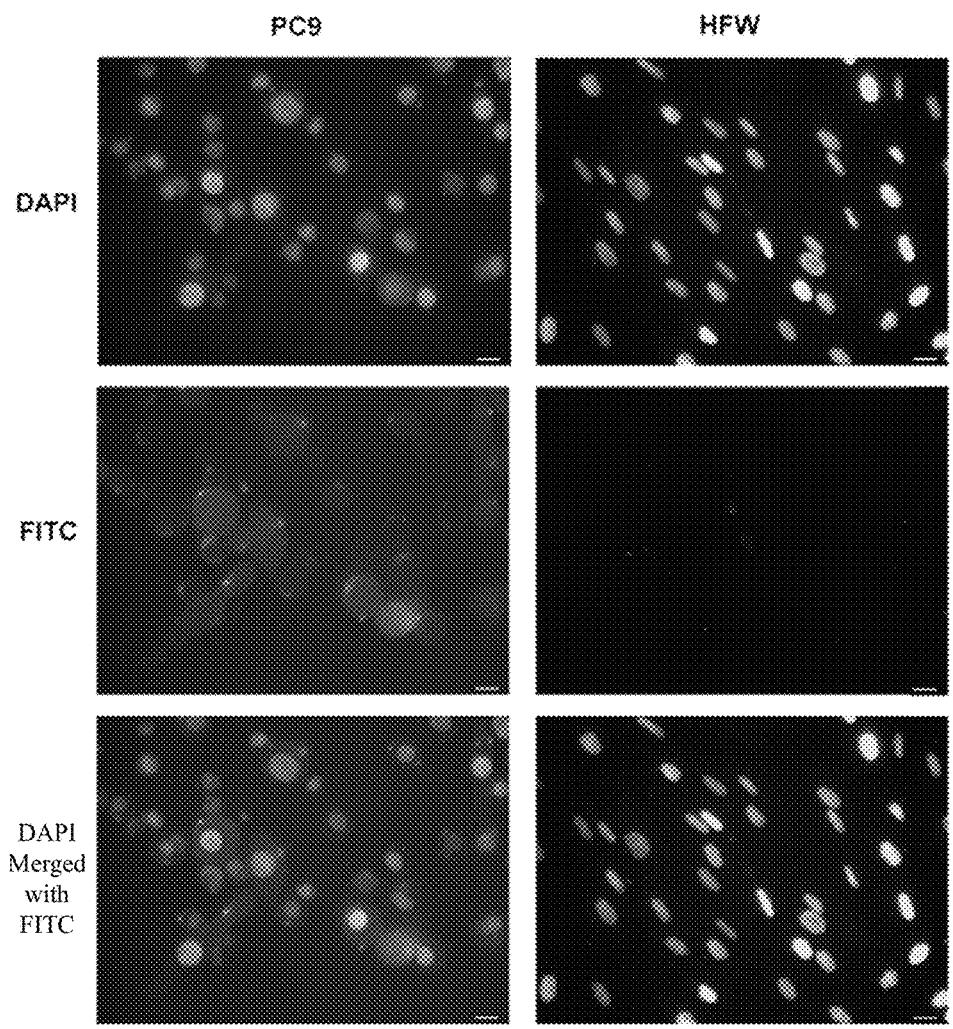
FIG. 5B shows results of immunofluorescence analysis for interaction of FITC-conjugated K4R2-Nal2-S1 peptide with PC9 and HFW cells. Cells were prestained with DAPI for nuclear detection, followed by FITC-K4R2-Nal2-S1 peptide (12 μM) treatment for 1 hour. DAPI and FITC were presented in blue and green signals under UV and blue light sources, respectively. All Scale bars=20 μm.

Phase-contrast microscopy showed that K4R2-Nal2-S1 treatment induced cellular swelling in PC9 but not in HFW cells (see FIG. 5A). Moreover, immunofluorescence analysis revealed that FITC-labeled K4R2-Nal2-S1 peptide treatment caused puncta formation on cell membrane in PC9, but not in HFW cells (see FIG. 5B). Accordingly, it is understood that K4R2-Nal2-S1 binds cell membrane, inducing cell death.

Figure 6:
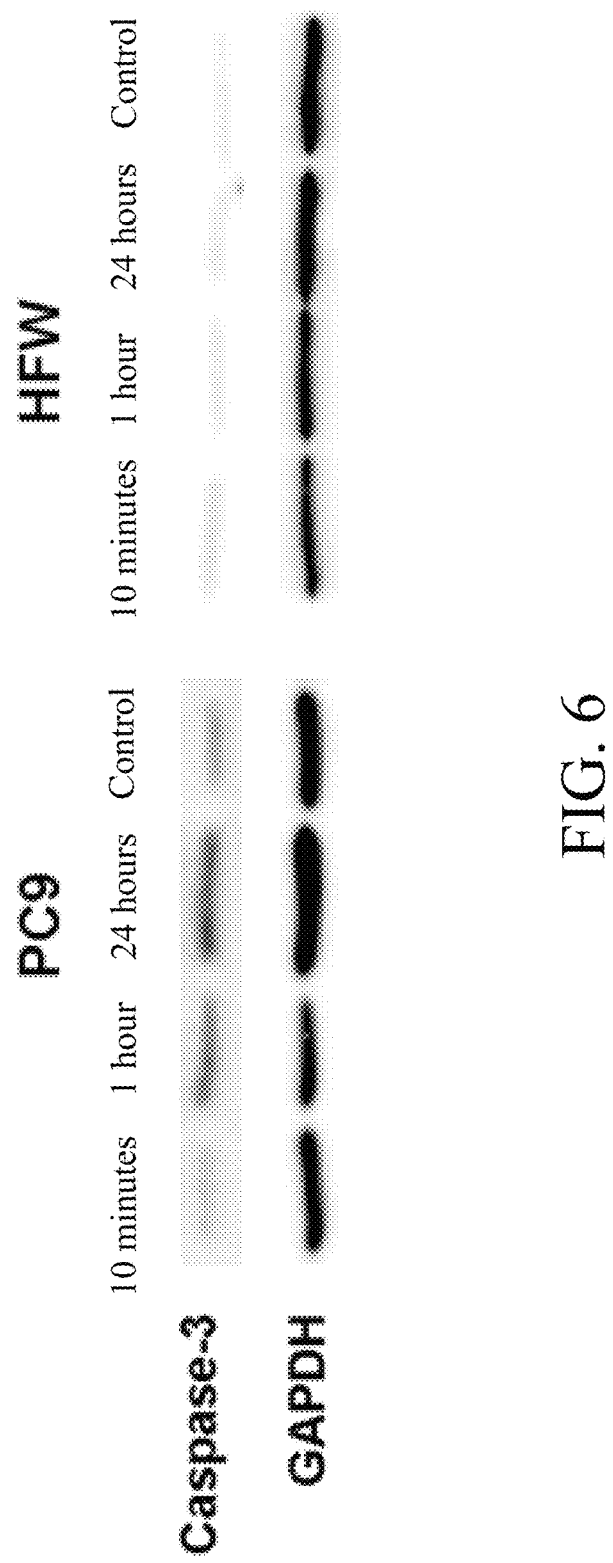
FIG. 6 shows Western blot analysis for activated caspase 3 expression to monitor cellular apoptosis in PC9 and HFW cells at the indicated time points. GAPDH served as a loading control.

Results of immunoblotting indicated that K4R2-Nal2-S1 peptide treatment activated caspase 3 in PC9 but not in HFW cells, suggesting the involvement of apoptosis in K4R2-Nal2-S1 mediated cell death (see FIG. 6).

The foregoing results indicate that K4R2-Nal2-S1 peptide preferentially binds cancer cells, causing apoptotic cell death.

5. Inhibiting Lung Cancer Growth in Xenograft Mouse Model

Figure 7A:
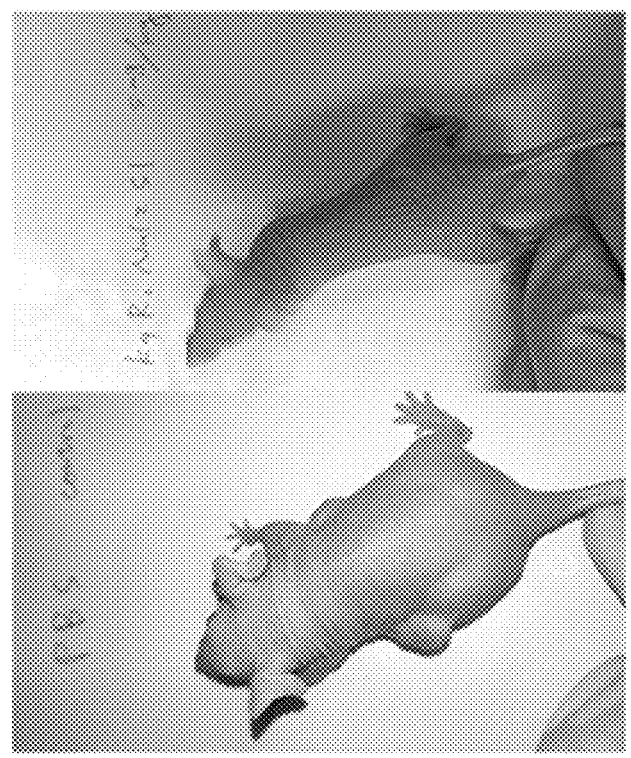
FIG. 7A shows dorsal sides of male nude mice subcutaneously (s.c.) injected with PC9 human lung cancer cells and intravenously (i.v.) injected with K4R2Nal2-S1 peptide (right) or PBS control (left) at the 46th day after cancer cell implantation (5 days for tumor growth, 40 days for treatment, photographed on the 46th day)
Figure 7B:
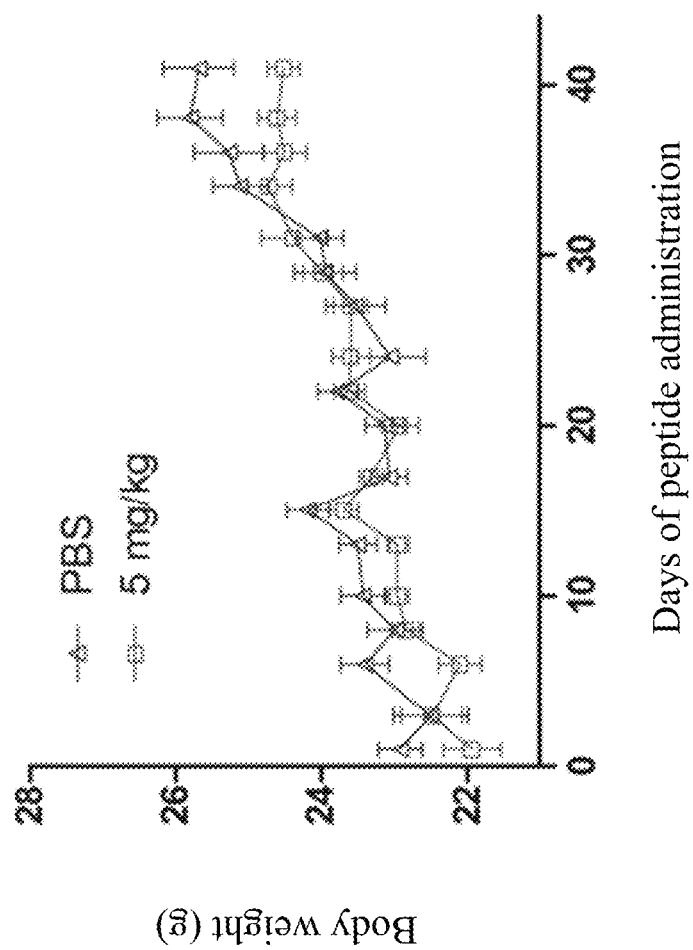
FIGS. 7B and 7C show mice body weight (FIG. 7B) and tumor volume (FIG. 7C) of the mice monitored over the time period as indicated in FIG. 7A.
Figure 7C:
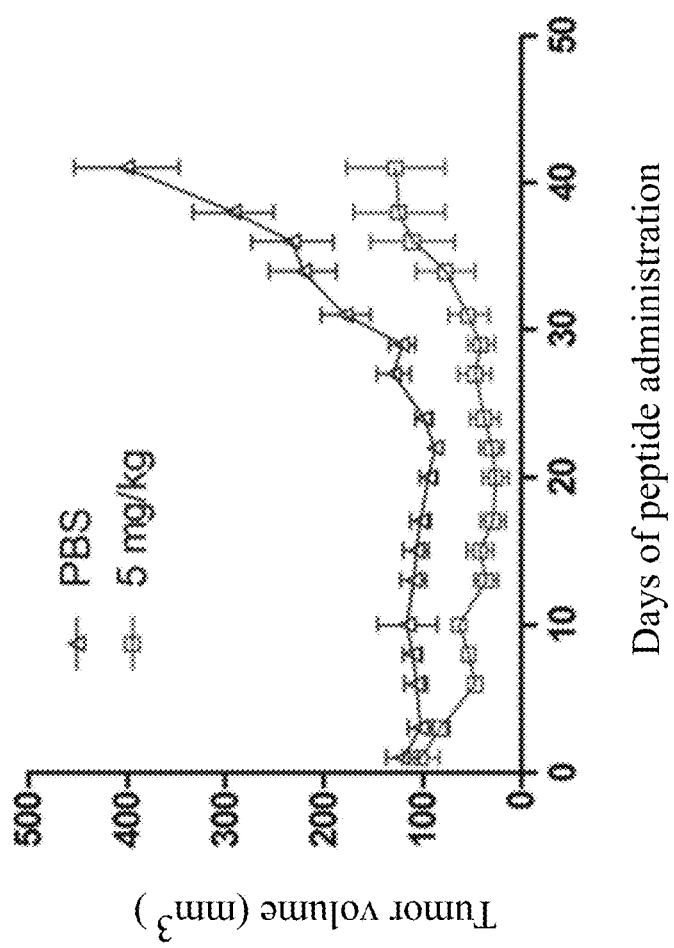

To evaluate the anticancer effect of K4R2Nal2-S1 peptide in vivo, PC9 cells were implanted subcutaneously to nude mice (see FIG. 7A) and followed by K4R2-Nal2-S1 injection via the intravenous route, at a dose of 5 mg/kg, three times weekly (FIGS. 7B and 7C).

Figure 7D:
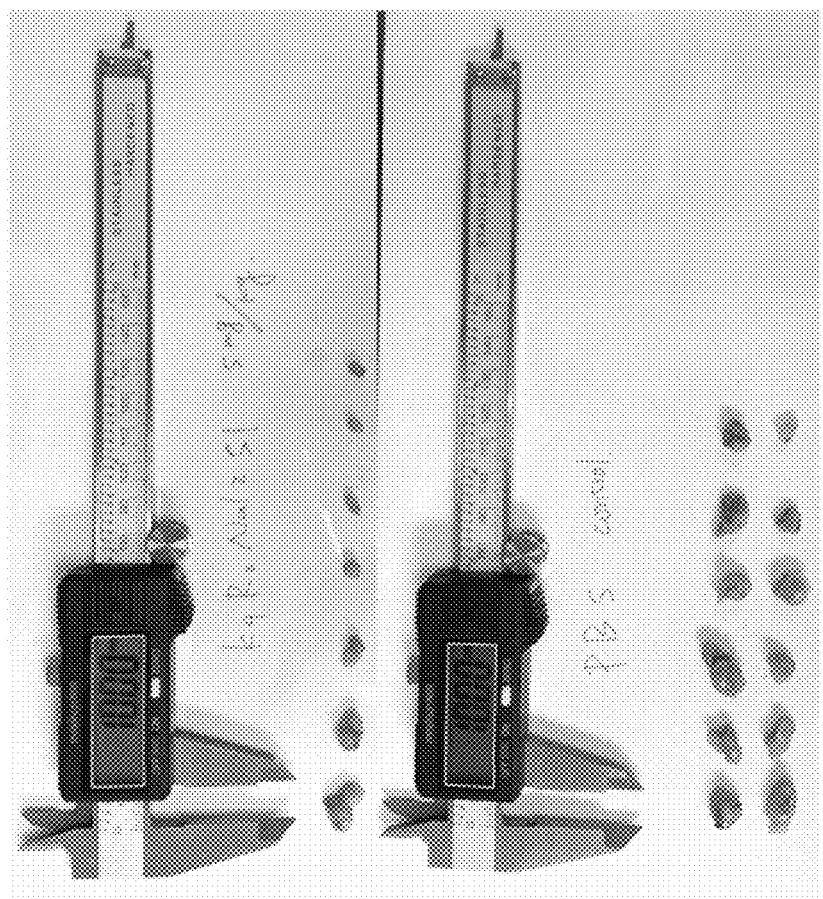
FIG. 7D shows exposed tumors (mice were sacrificed at the 46th day after cancer cell implantation) of mice treated with K4R2Nal2-S1 peptide (upper) or PBS (lower). 12 exposed tumors were found in the PBS group (6 mice×2 side implantation), but only 7 exposed tumors were found in the K4R2Nal2-S1 peptide treatment group.
Figure 7E:
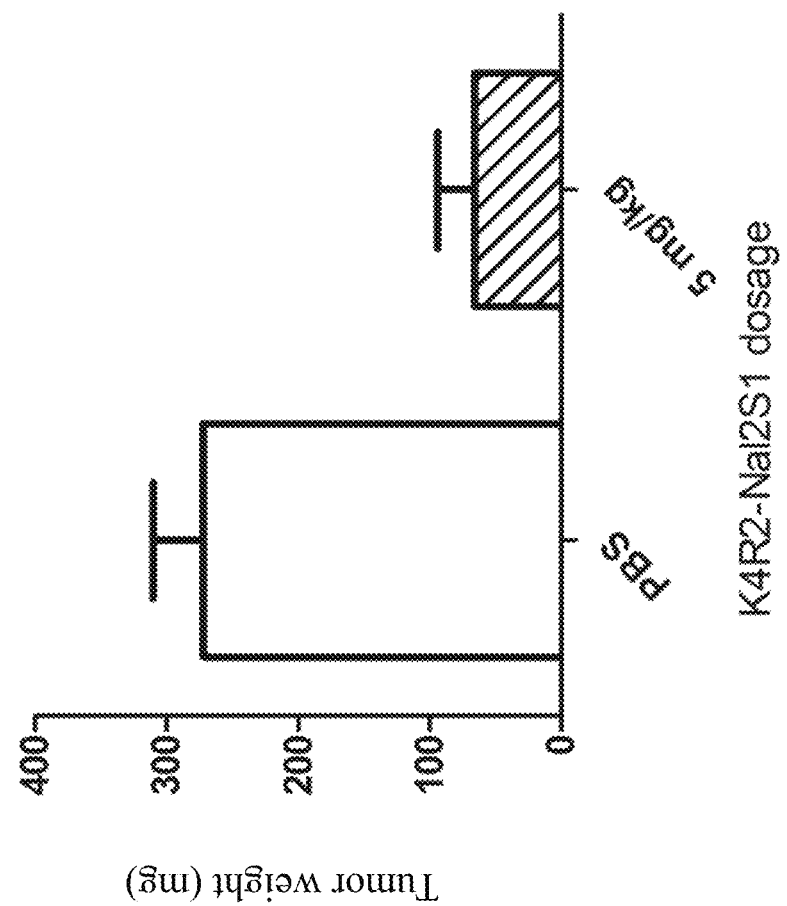
FIG. 7E shows total tumor weight for mice treated with K4R2Nal2-S1 peptide and total tumor weight for mice treated with PBS in FIG. 7D.

During the administration, body weight loss was not found in K4R2Nal2-S1 peptide treated group (FIG. 7B); however, a significant inhibition in tumor growth was observed in the mice treated with K4R2-Nal2-S1 (FIG. 7C). K4R2-Nal2-S1 peptide treatment also decreased the volume and weight of tumors harvested 40 days after injection (FIGS. 7D and 7E).

The results mentioned above clearly show that K4R2-Nal2-S1 peptide treatment attenuates the xenograft tumor growth.

To examine the involvement of necrosis and apoptosis in K4R2Nal2-S1 peptide mediated anticancer effect, lung tumors generated in the xenograft mouse model were excised and analyzed by Hematoxylin and eosin (H&E) staining and immunohistochemistry for cleaved PARP, a marker for cell apoptosis.

Figure 8:
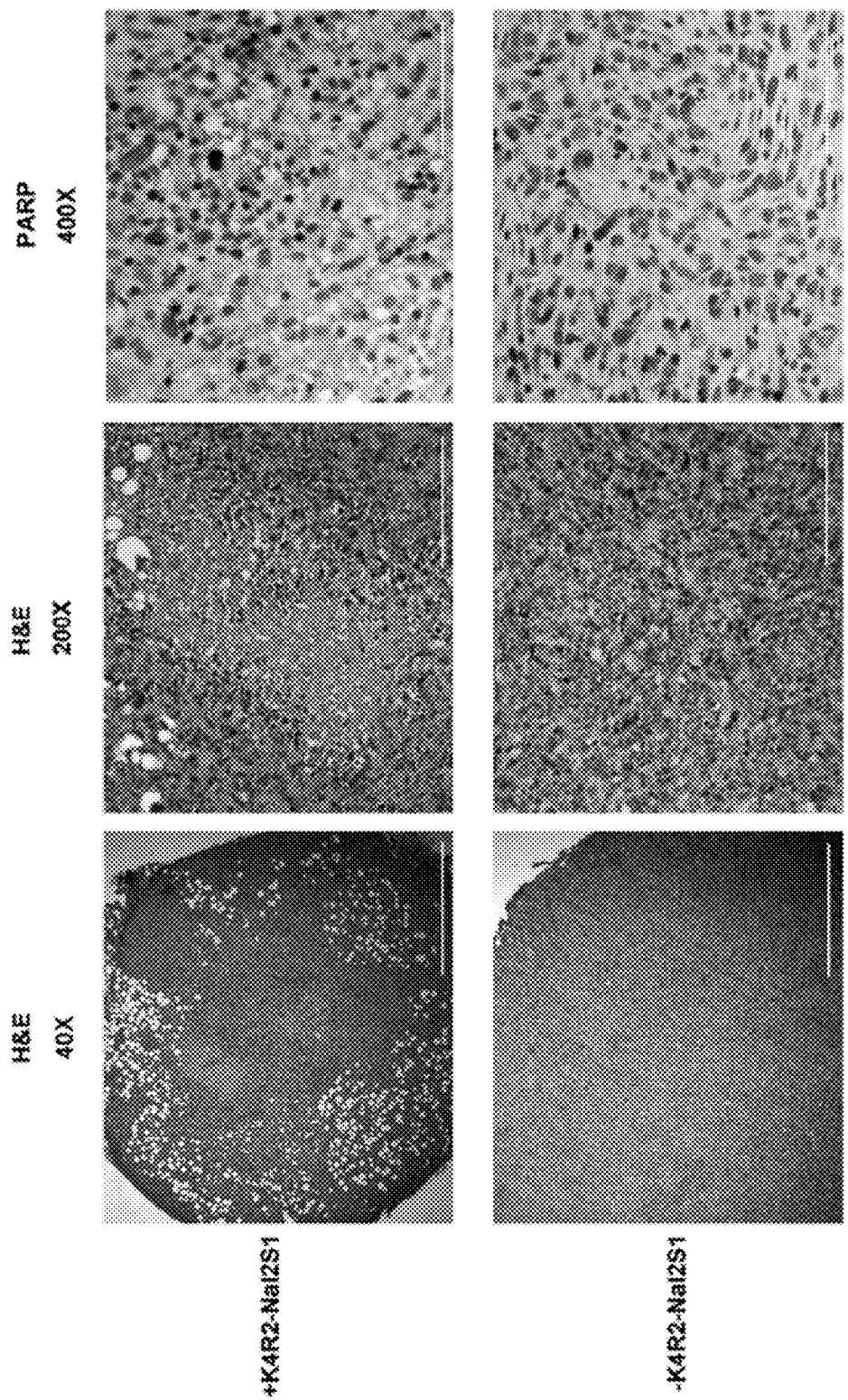
FIG. 8 shows excised xenografted tumors from the mice in FIGS. 4A and 5B which were subjected to H&E staining and immunohistochemical assay for cleaved PARP expression to monitor cellular apoptosis. Scale bars=500 μm, 100 μm, and 50 μm (40×, 200×, and 400×), respectively.

The Hematoxylin and eosin (H&E) staining showed the presence of large scale of necrosis regions in K4R2-Nal2-S1 peptide treated cancers but not in those treated with PBS (FIG. 8). Immunohistochemistry indicated increased expression of cleaved PARP next to the necrosis regions in tumors under K4R2-Nal2-S1 peptide treatment. These data support the notion that K4R2Nal2-S1 peptide treatment inhibits tumor growth.

6. Cell Migration Assay (In Vitro Wound Healing Assay)

HaCaT cells (40,000) suspended in DMEM medium supplemented with 10% fetal bovine serum were seeded on each side of an ibidi culture insert (ibidi, Germany). Inserts were placed into 24-well plate. After incubated at 37° C. and 5% $CO_2$ overnight, inserts were removed and 1 ml of serum-free DMEM medium supplemented with different concentrations of peptide was added. Medium without peptide and with 100 ng/ml EGF (epidermal growth factor) were negative and positive controls. At 0, 12 and 24 h, the images of injury area were observed using the Inverted Fluorescent Microscope Zeiss/Observer.Z1 (10×). Wound area was estimated by Adobe Photoshop. The repairing rate was calculated: repairing rate=(area$_{t0}$−area$_{t12,24}$)/area$_{t0}$, wherein t represents time.

Figure 9A:
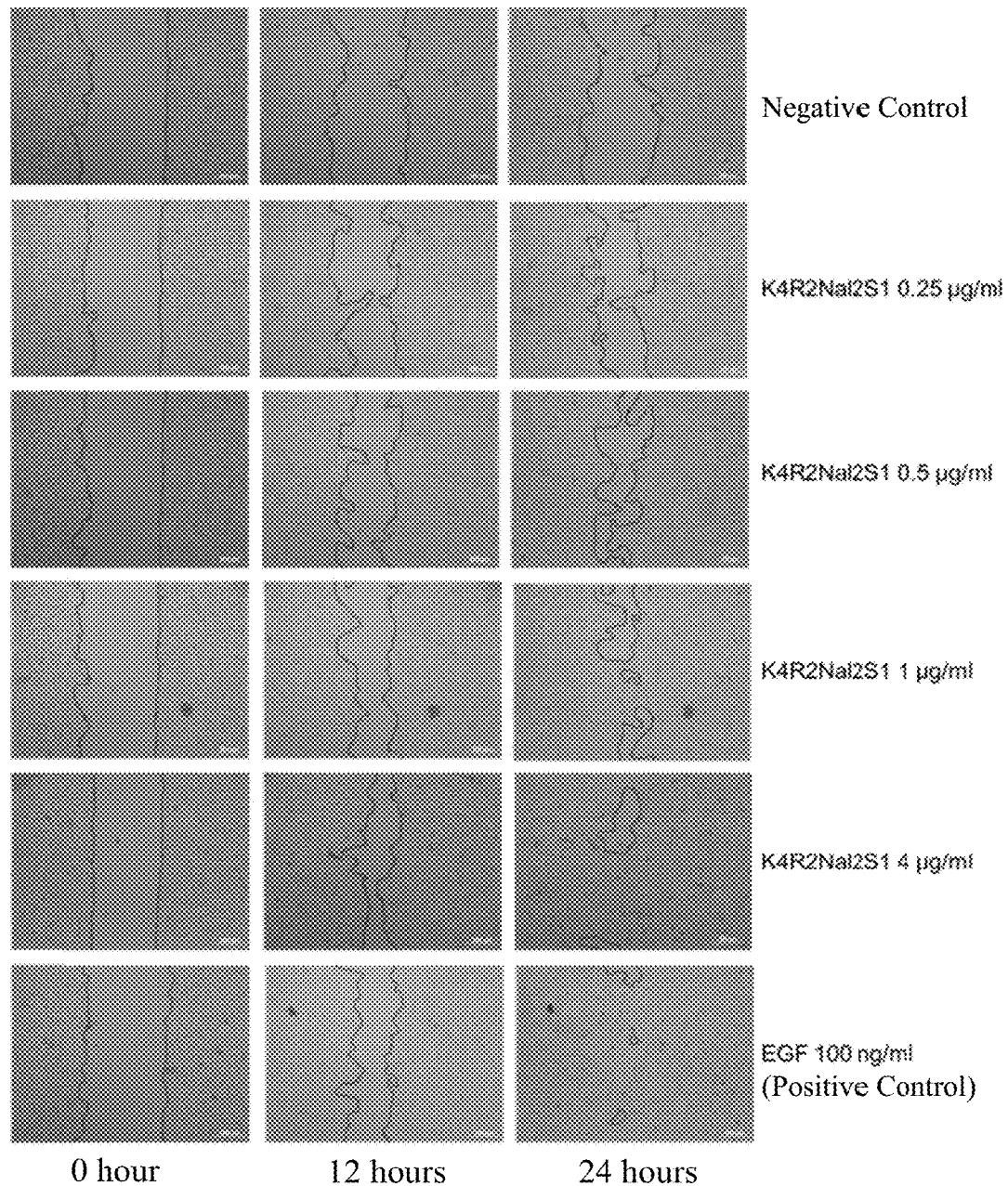
FIG. 9A shows images for different testing groups observed at 0 hour, 12 hour and 24 hour in the cell migration assay.
Figure 9B:
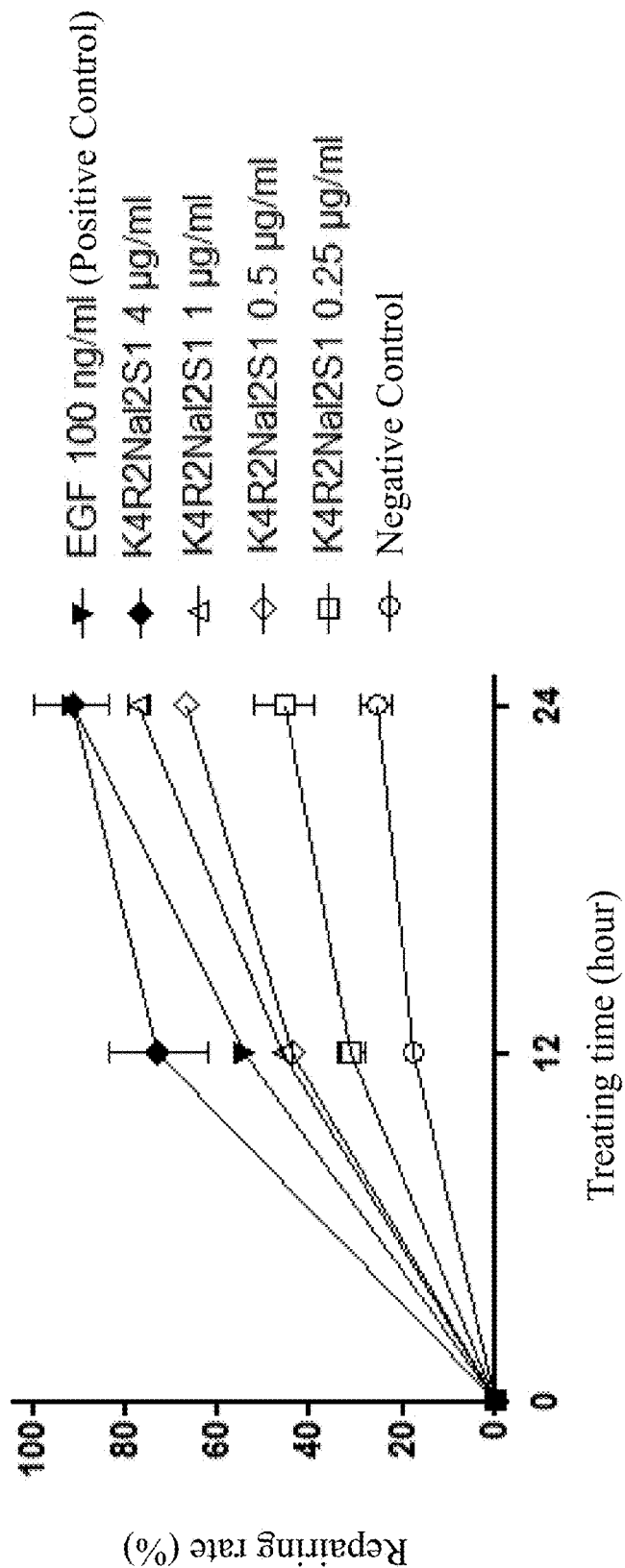
FIG. 9B shows repairing rates for different testing groups in the cell migration assay.

FIG. 9A shows images for different testing groups observed at 0 hour, 12 hour and 24 hour in the cell migration assay. FIG. 9B shows repairing rates for different testing groups in the cell migration assay.

According to FIGS. 9 and 9B, it is clearly understood that, as compared to the negative control group, different concentrations of K4R2-Nal2-S1 peptide all have better effects of wound healing. In other words, K4R2-Nal2-S1 performs an activity that enhances wound healing.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A peptide with antimicrobial, anticancer and/or wound-healing promoting activities, comprising:
   an α-helix peptide; and
   a short peptide consisting of 6 positively charged amino acids, connected to an N-terminus of the α-helix peptide to form the peptide with antimicrobial, anticancer and/or wound-healing promoting activities, wherein the positively charged amino acids are a combination of 4 lysines and 2 arginines,
   wherein the total length of the peptide with antimicrobial, anticancer and/or wound-healing promoting activities is about 10-20 amino acids.

2. The peptide with antimicrobial, anticancer and/or wound-healing promoting activities as claimed in claim 1, wherein the α-helix peptide has one or more non-natural amino acids.

3. The peptide with antimicrobial, anticancer and/or wound-healing promoting activities as claimed in claim 2, wherein the non-natural amino acid or each of the non-natural amino acids is independently selected from the group consisting of β-naphthylalanine (Nal), (benzothien-3-yl)alanine (Bal), diphenylalanine (Dip), (4,4'-biphen-yl) alanine (Bip), (anthracen-9-yl) alanine (Ath) and (2,5,7-tri-tert-butyl-indol-3-yl) alanine (Tht).

4. The peptide with antimicrobial, anticancer and/or wound-healing promoting activities as claimed in claim 2, wherein the non-natural amino acid or the non-natural amino acids is/are β-naphthylalanine.

5. The peptide with antimicrobial, anticancer and/or wound-healing promoting activities as claimed in claim 2, wherein the non-natural amino acids are completely continuously arranged, partially continuously arranged or non-continuously arranged.

6. The peptide with antimicrobial, anticancer and/or wound-healing promoting activities as claimed in claim 2, wherein the non-natural amino acids are completely continuously arranged.

7. The peptide with antimicrobial, anticancer and/or wound-healing promoting activities as claimed in claim 6, wherein the non-natural amino acids are located at an N-terminus of the α-helix peptide and directly connect to the short peptide, or are located at a C-terminus of the α-helix peptide.

8. The peptide with antimicrobial, anticancer and/or wound-healing promoting activities as claimed in claim 6, wherein the non-natural amino acids are located at the N-terminus of the α-helix peptide and directly connect to the short peptide.

9. The peptide with antimicrobial, anticancer and/or wound-healing promoting activities as claimed in claim 8, wherein the α-helix peptide has two non-natural amino acids.

10. The peptide with antimicrobial, anticancer and/or wound-healing promoting activities as claimed in claim 8, wherein the two non-natural amino acids are both β-naphthylalanine.

11. The peptide with antimicrobial, anticancer and/or wound-healing promoting activities as claimed in claim 2, wherein the α-helix peptide comprises SEQ ID NO: 1.

12. The peptide with antimicrobial, anticancer and/or wound-healing promoting activities as claimed in claim 1, wherein from the N-terminus to the C-terminus of the short peptide, the positively charged amino acids are 4 lysines and 2 arginines in order.

13. The peptide with antimicrobial, anticancer and/or wound-healing promoting activities as claimed in claim 1, wherein the sequence of the peptide with antimicrobial, anticancer and/or wound-healing promoting activities comprises the sequence of SEQ ID NO: 2.

14. The peptide with antimicrobial, anticancer and/or wound-healing promoting activities as claimed in claim 1, wherein the sequence of the peptide with antimicrobial, anticancer and/or wound-healing promoting activities is the sequence of SEQ ID NO: 2.

15. The peptide with antimicrobial, anticancer and/or wound-healing promoting activities as claimed in claim 1, wherein an N-terminus of the peptide with antimicrobial, anticancer and/or wound-healing promoting activities is acetylated.

16. The peptide with antimicrobial, anticancer and/or wound-healing promoting activities as claimed in claim 1, wherein a C-terminus of the peptide with antimicrobial, anticancer and/or wound-healing promoting activities is amidated.

17. The peptide with antimicrobial, anticancer and/or wound-healing promoting activities as claimed in claim 1, wherein an N-terminus and a C-terminus of the peptide with antimicrobial, anticancer and/or wound-healing promoting activities are acetylated and amidated, respectively.

18. The peptide with antimicrobial, anticancer and/or wound-healing promoting activities as claimed in claim 17, wherein the sequence of the peptide with antimicrobial, anticancer and/or wound-healing promoting activities is the sequence of SEQ ID NO: 2.

19. A pharmaceutical composition, comprising:
the peptide with antimicrobial, anticancer and/or wound-healing promoting activities as claimed in claim 1; and
a pharmaceutically acceptable carrier or salt,
wherein the pharmaceutical composition has antimicrobial, anticancer and/or wound-healing promoting activities, and has no influence on a normal cell.

20. The pharmaceutical composition as claimed in claim 19, wherein the α-helix peptide comprises SEQ ID NO: 1.

21. The pharmaceutical composition as claimed in claim 19, wherein the sequence of the peptide with antimicrobial, anticancer and/or wound-healing promoting activities comprises the sequence of SEQ ID NO: 2.

22. The pharmaceutical composition as claimed in claim 19, wherein the N-terminus and the C-terminus of the peptide with antimicrobial, anticancer and/or wound-healing promoting activities are acetylated and amidated, respectively.

23. The pharmaceutical composition as claimed in claim 19, wherein the pharmaceutical composition has antimicrobial activity against a Gram-positive bacterium and/or a Gram-negative bacterium.

24. The pharmaceutical composition as claimed in claim 23, wherein the Gram-positive bacterium is *Staphylococcus aureus*.

25. The pharmaceutical composition as claimed in claim 23, wherein the Gram-negative bacterium comprises *Escherichia coli* or *Pseudomonas aeruginosa*.

26. The pharmaceutical composition as claimed in claim 23, wherein the pharmaceutical composition has anticancer activity against a lung cancer cell, an oral cancer cell, a prostate cancer cell, a breast cancer cell, a liver cancer cell or a pancreas cancer cell.

27. A method for preparing a pharmaceutical composition with antimicrobial, anticancer and/or wound-healing promoting activities, comprising:
providing an effective amount of the peptide with antimicrobial, anticancer and/or wound-healing promoting activities as claimed in claim 1, serving as an active ingredient, in preparation of a pharmaceutical composition with antimicrobial, anticancer and/or wound-healing promoting activities,
wherein the pharmaceutical composition is capable of inhibiting a microorganism, inhibiting a cancer cell, and/or promoting wound-healing.

28. The method for preparing a pharmaceutical composition with antimicrobial, anticancer and/or wound-healing promoting activities as claimed in claim 27, wherein the α-helix peptide comprises SEQ ID NO: 1.

29. The method for preparing a pharmaceutical composition with antimicrobial, anticancer and/or wound-healing promoting activities as claimed in claim 27, wherein the sequence of the peptide with antimicrobial, anticancer and/or wound-healing promoting activities is the sequence of SEQ ID NO: 2.

30. The method for preparing a pharmaceutical composition with antimicrobial, anticancer and/or wound-healing promoting activities as claimed in claim 27, wherein the N-terminus and the C-terminus of the peptide with antimicrobial, anticancer and/or wound-healing promoting activities are acetylated and amidated, respectively.

31. A method for inhibiting a microorganism, inhibiting a cancer cell, and/or promoting wound-healing, comprising:
administering the pharmaceutical composition as claimed in claim 19 to a subject in need thereof.

* * * * *